United States Patent
Funk

(10) Patent No.: US 9,014,328 B2
(45) Date of Patent: *Apr. 21, 2015

(54) METHOD AND APPARATUS FOR ADVANCED X-RAY IMAGING SYSTEMS

(71) Applicant: Triple Ring Technologies, Inc., Newark, CA (US)

(72) Inventor: Tobias Funk, Martinez, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,123

(22) Filed: Jul. 4, 2014

(65) Prior Publication Data

US 2014/0321606 A1    Oct. 30, 2014

Related U.S. Application Data

(63) Continuation of application No. 13/440,394, filed on Apr. 5, 2012, now Pat. No. 8,774,351.

(60) Provisional application No. 61/472,128, filed on Apr. 5, 2011.

(51) Int. Cl.
*A61B 6/06* (2006.01)
*A61B 6/00* (2006.01)
*A61B 6/03* (2006.01)

(52) U.S. Cl.
CPC .............. *A61B 6/587* (2013.01); *A61B 6/032* (2013.01); *A61B 6/06* (2013.01); *A61B 6/4007* (2013.01); *A61B 6/4028* (2013.01); *A61B 6/4064* (2013.01); *A61B 6/4241* (2013.01); *A61B 6/4435* (2013.01); *A61B 6/4488* (2013.01)

(58) Field of Classification Search
CPC .......... A61B 6/587; A61B 6/032; A61B 6/06; A61B 6/4007; A61B 6/4028; A61B 6/4064; A61B 6/4241; A61B 6/4435; A61B 6/4488
USPC ................... 378/4, 9, 57, 143, 147, 161, 205
See application file for complete search history.

(56) References Cited

U.S. PATENT DOCUMENTS

| | | | |
|---|---|---|---|
| 7,023,950 B1 * | 4/2006 | Annis | 378/2 |
| 7,835,488 B2 * | 11/2010 | Heuscher et al. | 378/11 |
| 2003/0043958 A1 * | 3/2003 | Mihara et al. | 378/4 |

* cited by examiner

*Primary Examiner* — Irakli Kiknadze
(74) *Attorney, Agent, or Firm* — Joseph T. Lin; Sabrina N. David

(57) ABSTRACT

The present invention pertains to an apparatus and method for X-ray imaging a human patient. A vacuum bell bonded to an X-ray radiation-permeable window that can emit X-ray radiation from a plurality of spots located 1 cm from its edge, a collimator, and a detector are used. A ring of stationary X-ray sources can also be used with a stationary collimator and a rotating slot collimator and detector. An X-ray beam can be aligned in an X-ray system by establishing a position of the beam with respect to a moving collimator at a number of points in time, monitoring the velocity of the collimator, navigating the beam to a calculated position of a hole in the collimator, and correcting the alignment of the beam based on the location of the beam on the detector.

20 Claims, 12 Drawing Sheets

METHOD AND APPARATUS FOR ADVANCED X-RAY IMAGING SYSTEMS

RELATED U.S. APPLICATION

This application is a continuation application claiming priority from the co-pending U.S. non-provisional patent application Ser. No. 13/440,394, entitled "METHOD AND APPARATUS FOR ADVANCED X-RAY IMAGING SYSTEMS," with filing date Apr. 5, 2012. U.S. non-provisional patent application Ser. No. 13/440,394 claims priority to U.S. provisional patent application Ser. No. 61/472,128, entitled "Computed Tomography Systems With Stationary Source," with filing date Apr. 5, 2011, all of which are hereby incorporated by reference in its entirety.

FIELD OF THE INVENTION

The present invention pertains to x-ray imaging systems. The present invention also pertains to x-ray computed tomography systems.

BACKGROUND

Computed tomography (CT) is undeniably an important technology in modern medicine. CT is used throughout screening, treatment, and follow-up examinations; it is not uncommon for a patient to receive ten CT scans during this time.

In light of the increasingly frequent use of CT for cancer imaging, high radiation dose from CT scans are concerning. There is strong scientific evidence that the elevated dose exposures as found in CT are leading to a significantly increased risk of cancer, especially in young patients. The National Academy of Sciences BEIR V (Biological Effects of Ionizing Radiations) committee and the ICRP (International Commission on Radiological Protection) have reported that for a single acute radiation exposure in children the lifetime attributable cancer mortality risk is as high as 14% per Gy. This risk goes down with age, but is still in the 2-8% range in the 30-50 age group. Importantly, recent reports on the biological effects of radiation reaffirm the utility of the linear no-threshold model of radiation risk for solid cancers. Brenner et al. have shown that the average dose of a single CT scan leads to about 5 cancer deaths in 10000 patients depending on the age of the patient and type of exam performed.

The magnitude of the problem is worsening due to the large number of CT scans performed every year (62 million in the United States in 2006). While CT accounts for only 17% of imaging procedures using radiation, it delivers 49% of the overall dose. The NCI (National Cancer Institute) website states: "CT is the largest contributor to medical exposure to the U.S. population."

CT is currently being investigated as a screening tool for early, asymptomatic cancer detection. A recent publication in the New England Journal of Medicine by the International Early Lung Cancer Action Program Investigators concludes: "Annual spiral CT screening can detect lung cancer that is curable." The NCI is currently conducting the National Lung Cancer Screening Trial (NLST) with the objective to qualify CT and other X-ray modalities for lung-cancer screening. One potential outcome of this trial is the recommendation to screen a large population for lung cancer with CT, thus increasing the radiation exposure to a large group of asymptomatic people. In fact, a recent press release reports that NLST "found 20 percent fewer lung cancer deaths among trial participants screened with low-dose helical CT." Additionally, NCI is funding an R01 grant to develop an iterative-reconstruction algorithm for dose reduction in CT lung-cancer screening. Thus, the prospect of CT use in cancer screening warrants investigating ways to make CT more dose efficient.

Colorectal cancer, the fourth leading cause of cancer deaths worldwide, is largely preventable with appropriate screening. Optical colonoscopy is the method of choice. However, the nature of the exam has led to low compliance with the recommended screening intervals. Virtual colonoscopy with CT is emerging as an alternative that potentially could lead to much higher compliance rates. For example, for President Obama's yearly health checkup, virtual colonoscopy was chosen over optical colonoscopy. Again, if virtual colonoscopy gains traction as a screening tool, a large number of asymptomatic people will receive regular CT scans with high radiation exposure.

Another area of immense concern is pediatric cancer imaging. A recent study by Robbins evaluates the treatment protocols by the Children's Oncology Group that are typically used in the United States. The study shows that throughout diagnosis, treatment, and follow-up periods for childhood cancers such as neuroblastoma, Wilms tumor, Ewing sarcoma and lymphoblastic lymphoma, the radiation dose from imaging studies ranges between 109 and 152 mSv. The radiation dose is mostly from CT with the evaluated cases involving more than 15 CT scans each. Based on the BEIR V and ICRP reports, the lifetime risk of these children developing a fatal cancer is in the 1-2% range. While pediatric cancer is a small fraction in the overall cancer problem, children are a particularly vulnerable group.

These examples highlight the broader problem of high radiation exposure in cancer imaging with CT. Therefore, it is desirable to reduce radiation dose in CT to continue the impressive success of CT in fighting cancer and at the same time reduce the risk of causing cancer with the very same modality.

Furthermore, modern computed tomography (CT) scanners have the goal of covering a large volume of the patient in a single rotation at very fast rotation speeds. This objective is driven by demands of cardiac CT to cover the entire organ in less than a heartbeat. Impressive results have been achieved with the current generation of CT scanners. However, the downside of this development is the increased dose to the patient, the increase in scatter, and the degradation of image quality in the outer slices due to cone beam artifacts. In particular, the increased dose in medical imaging has come under scrutiny, with several published studies documenting the elevated risk of cancer resulting from the radiation involved in medical imaging.

CT manufacturers are exploring a variety of methods to reduce this dose while maintaining image quality. However, these improvements are expected to be minor compared to that which may be gained by an alternative CT system concept, inverse-geometry CT (IGCT). Conventional point source CT utilizes a single focal spot X-ray source and a large-area detector, whereas IGCT utilizes a large-area, multi-focal spot X-ray source and a small-area detector. IGCT offers higher dose efficiency and faster acquisition times than state-of-the-art conventional point source CT systems. Thus, IGCT has the potential to overcome disadvantages with conventional point source CT and significantly out-perform conventional point source CT scanners.

However, IGCT as currently realized in prototypes faces difficulties in implementation due to a large source array to be rotated at high speeds and significant challenges from high power and cooling requirements of the source.

What is needed is a CT imaging system capable of producing rapid high quality images. Furthermore, the CT imaging system should provide low radiation imaging.

SUMMARY

In one embodiment, an X-ray system for imaging a human patient is provided. A vacuum bell bonded to an X-ray radiation-permeable window that can emit X-ray radiation from a plurality of spots located 1 cm from its edge, a collimator, and detector are used. The radiation-permeable window and vacuum bell can be bonded with a brazed or electron beam-welded connection. The radiation-permeable window may be beryllium and may have a thin film tungsten target deposited on it. A second vacuum bell and radiation-permeable window can be used, and the first and second permeable windows can be in contact with each other.

In another embodiment, a ring of stationary X-ray sources with a stationary collimator and rotating slot collimator and detector are provided. The rotating slot collimator can span an arc between 60 and 160 degrees. The stationary collimator can have at least ten or between 10 and 50 slots, can have at least 10 slots perpendicular to the slots of the rotating collimator, and can comprise metal rings. The system can use cooling water to remove heat from the X-ray target and can be operated at full power for at least one hour. The system can use a sensor to monitor the velocity of the rotating collimator.

In another embodiment, an X-ray beam is aligned in an X-ray system by establishing a position of the beam with respect to a moving collimator at a number of points in time, monitoring the velocity of the collimator, navigating the beam to a calculated position of a hole in the collimator, and correcting the alignment of the beam based on the location of the beam on the detector. The position of the detector can be calculated using the initial position and velocity of the collimator. The centroid position of the X-ray beam on the detector can be determined and compared to its calculated value. The X-ray beam can be aborted if the X-ray beam is not aligned.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
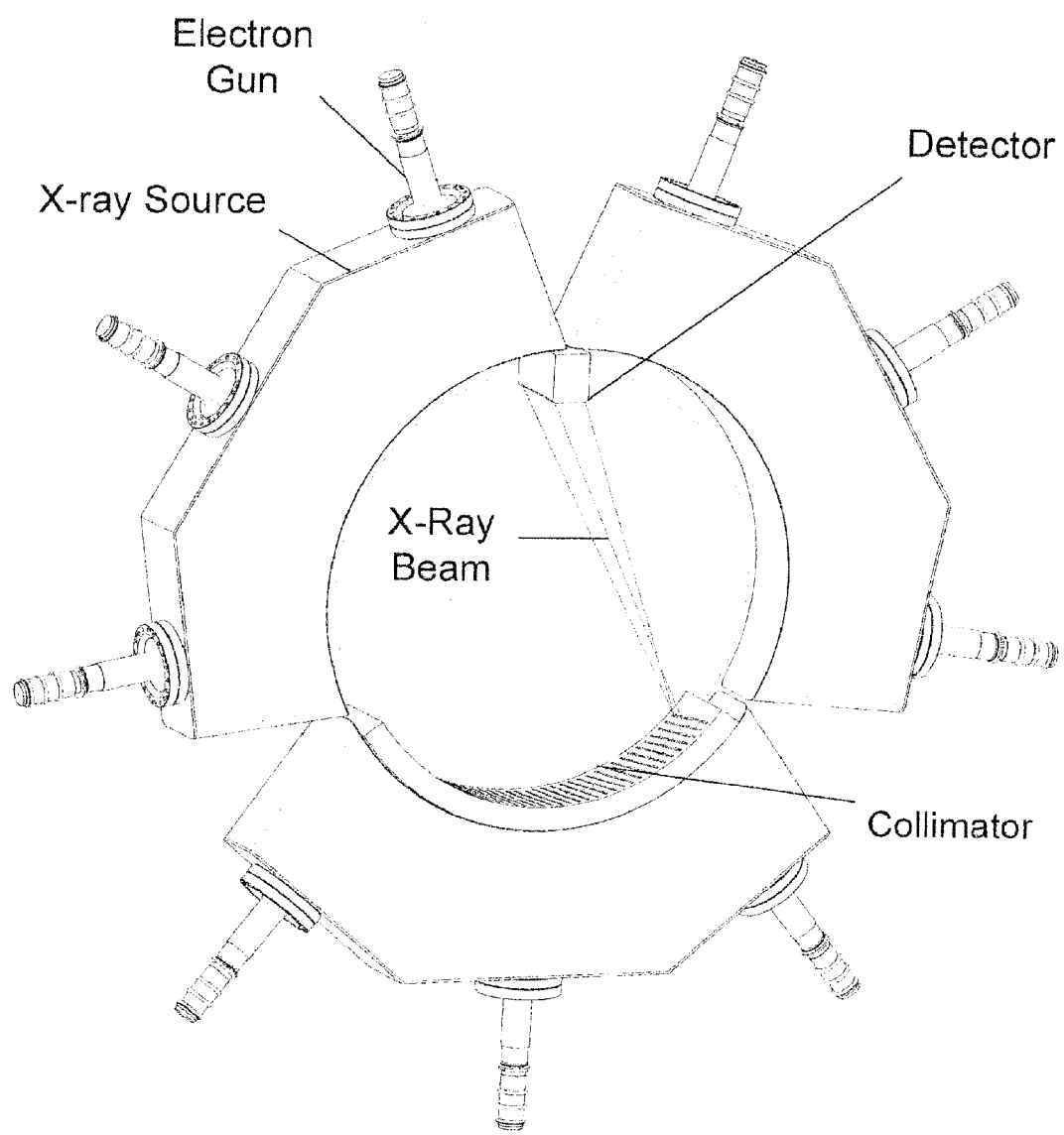
FIG. 1 is a diagram showing an exemplary fixed-source computed tomography imaging system of one embodiment of the present invention with three vacuum envelopes.

FIG. 1 is a diagram showing an exemplary fixed-source computed tomography imaging system of one embodiment of the present invention. Imaging system 100 comprises a ring of X-ray sources 101, 102, and 103 with an inner diameter of 1 m. The source ring can be made of three X-ray sources 101, 102, and 103 making a three-gap system as shown. For the three-gap system, there can be three separate source arrays, each containing three electron guns in a single vacuum envelope. Each of these source arrays can have a large-area tungsten transmission target. The source-spot locations can cover the full 360 degrees, except for a small gap of a few centimeters between each of these arrays. The axial extent of the source array can be 16 cm. There can be a fixed pre-collimator between the source arrays and the spinning ring. This pre-collimator defines the possible locations of the source-spots.

Within the ring of X-ray sources 101, 102, and 103 can be a rotating detector/collimator assembly. In one embodiment, only detector 110 and collimator 120 rotate. Collimator 120 can consist of an array of holes with each hole capable of illuminating the entire detector array. The center of the detector array can be diametrically across from the center of the collimator arc.

In operation, each row of the collimator 120 can have X-rays firing through its holes starting, for example, with the trailing hole and moving sequentially to the leading hole. The collimator rows can fire in sequence. A "super-view" can be obtained after all holes of all collimator rows have "fired". Other firing sequences are possible.

The detector elements can be read after a source-spot fires. The axial width of the detector array can also be 16 cm. By using the same axial width for both source and detector arrays there are no rays outside of the region of interest in the axial direction. Thus there is no unused exposure such as occurs in cone-beam systems.

Figure 2:
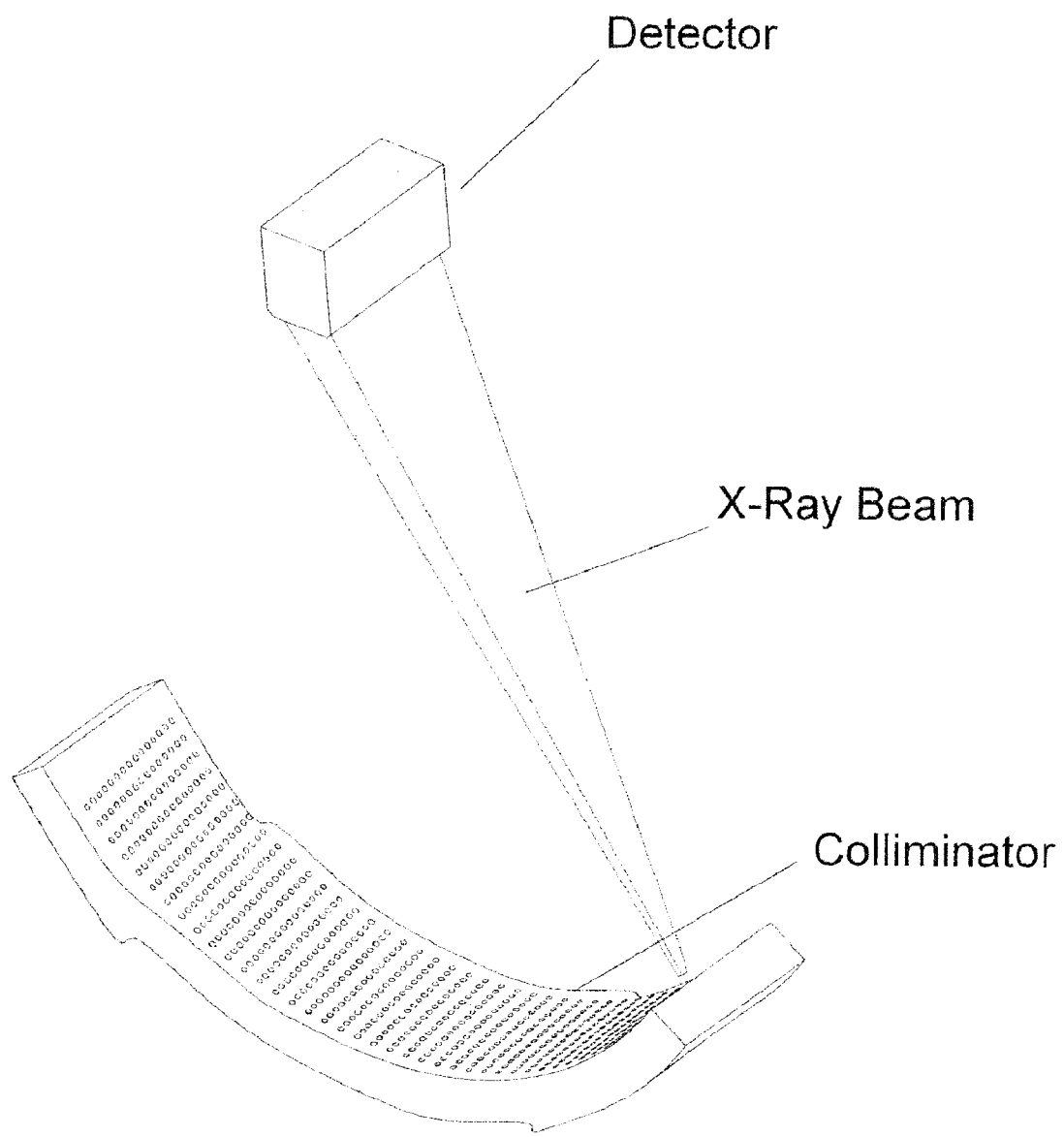
FIG. 2 is a diagram showing an exemplary isolated collimator-detector assembly of one embodiment of the present invention.

Imaging system 100 can have a large, 100 cm diameter, stationary ring of scanning X-ray source-spots. Inside the source-ring can be a rotating ring containing detector 110 and collimator 120. This rotating ring, or gantry, obtains power and outputs the detector signals through a slip-ring. FIG. 2 is a diagram showing an exemplary isolated collimator-detector assembly of one embodiment of the present invention. Collimator 220, which can be mounted opposite detector 110, can have a hole-pattern that focuses the X-rays onto detector 110. Detector 110 can be 6 cm by 16 cm and collimator 220 can span an arc of about 120 degrees and can have a width of 16 cm. Each collimator holes can illuminate the entire detector. This system design allows for rotation speeds of at least three rotations per second with image quality comparable to a conventional point source CT scanner.

Detector 110 can be a 6 cm by 16 cm detector. The detector ASIC can be modified to allow parallel current-integration readout and dual-energy acquisition.

Collimator 220 can be designed to attenuate 120 keV photons. It can consist of nearly 9,000 holes with a hole pitch of 2.3 mm. Each hole can be tapered and angled to project X-rays onto a 5-cm by 10-cm detector at a distance of 150 cm. Collimator 220 can also have approximately 600 holes projecting onto a 6-cm by 16-cm detector at a distance of 100 cm. Collimator 220 can be curved and have a larger area.

X-ray sources 101, 102, and 103 can be designed for continuous operation at 25 kW and at a tube voltage that can vary between 70 KVp and 120 kVp. The focal spot size can be 0.4 mm and the spot dwell time can be 1 μs with a duty cycle of 80%. The complete collimator can be scanned every 15 ms. X-ray sources 101, 102, and 103 can include a thin-film tungsten target layer deposited on a water-cooled 25-cm-diameter beryllium disc. The source power can be increased to 50 kW.

For a three-gap system, X-ray sources 101, 102, and 103 must cover a significantly larger target area. A large vacuum envelope that houses three guns in each source can be used. Each gun can illuminate a third of the target area. The use of three guns enables the entire target area to be illuminated. Different window material such as stainless steel and aluminum nitride can be used.

The projection data can be acquired as the collimator-detector assembly rotates around the patient. Collimator 120 can be located between the source array and the patient and source-spots are active only when behind collimator 120. Collimator 120 moves only a small angular increment during the time the scan of every designated hole in collimator 120 is completed. A complete scan of collimator 120 is described as a "superview". The maximum travel of detector 110 during an acquisition of a superview is one detector width. Therefore, a complete dataset can be obtained with as few as about 60 superviews.

High-weight, high-voltage, and high-power components of imaging system 100 can be removed from the challenging environment of the rotating gantry. Miniaturization of the high-voltage power supply is not required. High-power slip rings are not required. The X-ray source array can be cooled with hospital water, eliminating the conventional gantry-mounted radiator and increased air-conditioning requirement. Faster rotation times and faster volume acquisitions are possible. Overall reliability can be increased by the removal of many components, especially X-ray sources, from the high-G-force environment of the rotating gantry. A total source array area that is approximately three times larger than conventional point source systems can be required. However, the engineering necessary for this is greatly simplified compared to a rotating source array. Also, the cost per area for sources is significantly less than the cost per area of detectors. Thus, this can be also economically feasible.

Figure 3:
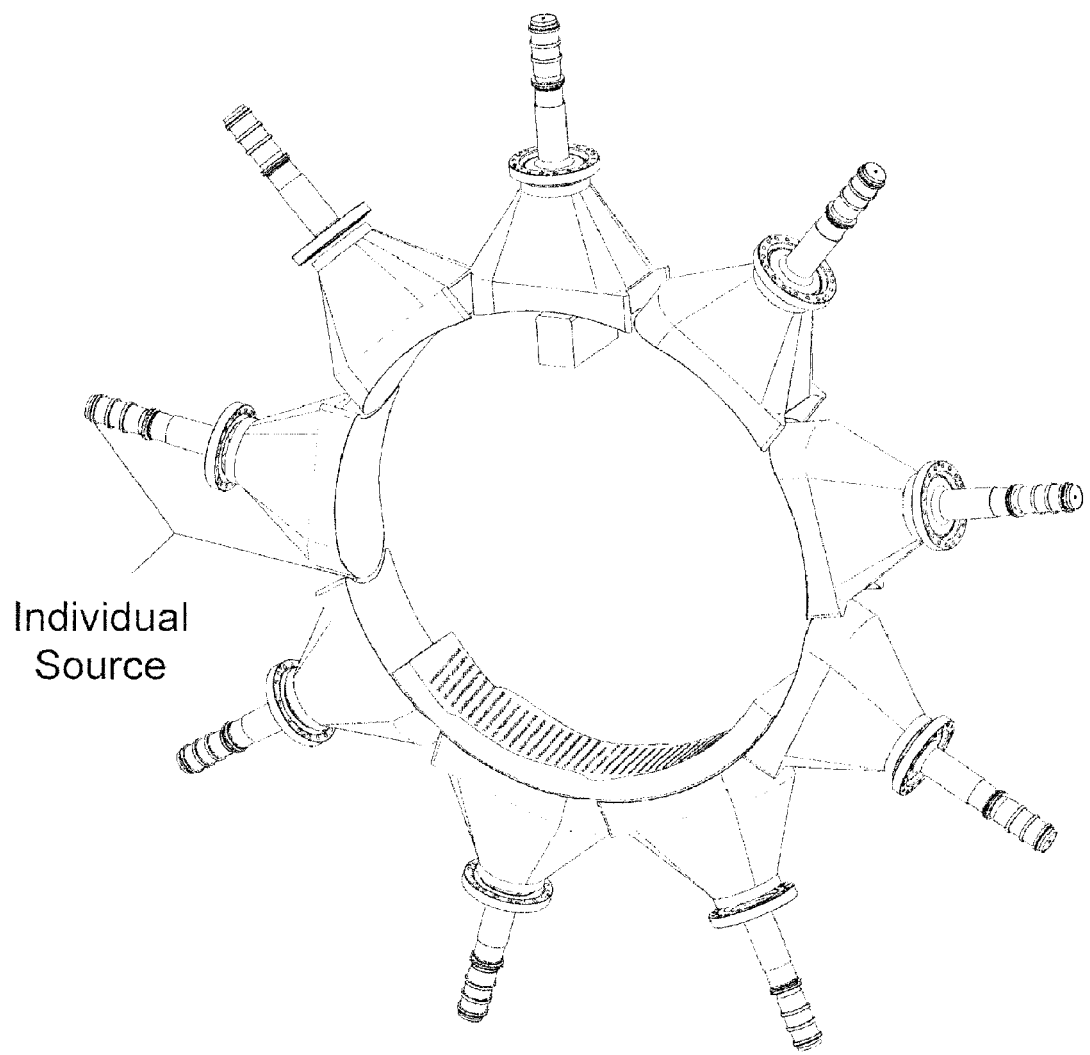
FIG. 3 is a diagram showing an exemplary fixed-source computed tomography imaging system of one embodiment of the present invention with nine vacuum envelopes.

FIG. 3 is a diagram showing an exemplary fixed-source computed tomography imaging system of one embodiment of the present invention with nine vacuum envelopes. In this embodiment, the source ring is made from nine individual X-ray sources forming a nine-gap system. There are nine separate source arrays, each containing a single electron gun in a single vacuum envelope. Each of the envelopes can have a 400 $cm^2$ source area.

Figure 4:
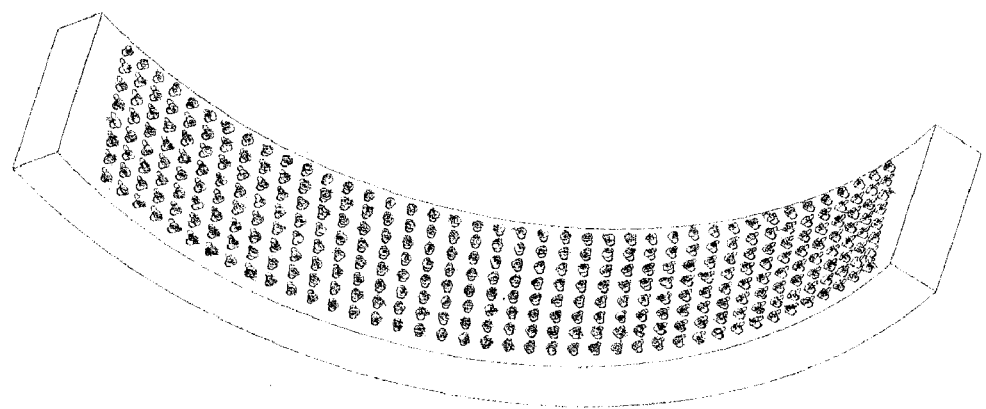
FIG. 4 is a diagram showing an exemplary uniform illumination pattern.
Figure 5:
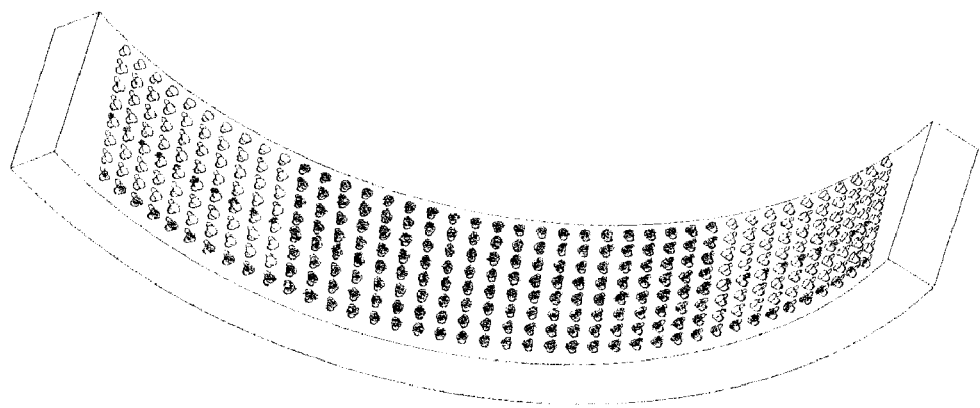
FIG. 5 is a diagram showing an exemplary illumination pattern that provides an increased flux in the central region of the collimator.
Figure 6:
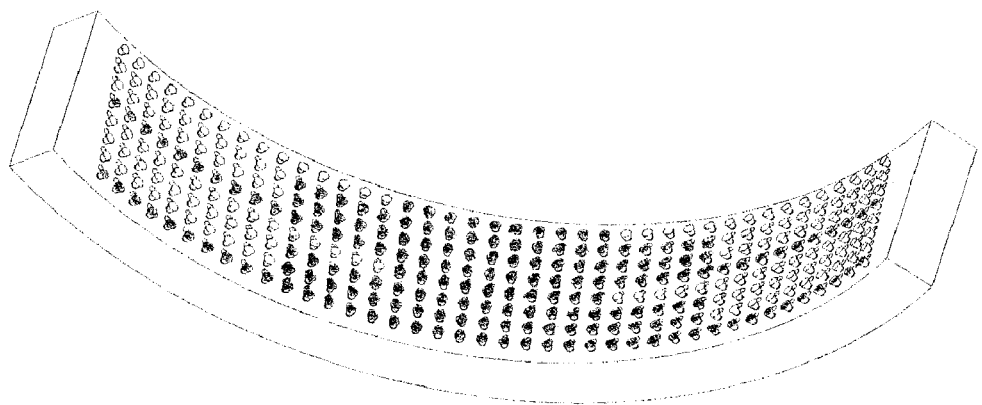
FIG. 6 is a diagram showing an exemplary illumination pattern that provides an increased flux in the central region of the collimator.

FIG. 4 is a diagram showing an exemplary uniform illumination pattern. FIG. 5 is a diagram showing an exemplary illumination pattern that provides an increased flux in the central region of the collimator. FIG. 6 is a diagram showing an exemplary illumination pattern that provides an increased flux in the central region of the collimator. FIG. 5 and FIG. 6 show patterns with increased intensity in the center. In practice the uniform and non-uniform patterns could be interleaved to ensure sampling completeness. The use of different illumination patterns can provide a two-dimensional adaptive filter. Several schemes for selecting the distribution of illumination are possible. Importantly, the illumination for one superview can be based on the results of the previous superview.

Iterative reconstruction methods can also be used. In particular, Maximum Likelihood Expectation Maximization (MLEM) is well suited for datasets from unconventional geometries. The algorithm is less prone to under-sampling artifacts and tends to reduce noise compared to standard algorithms.

One of the most critical design issues is the ability to produce enough photons to provide the desired image quality. Imaging system 100 acquires enough photons to produce an acceptable image. The detector array is 60 mm by 160 mm giving an area of about 96 $cm^2$. The duty cycle (the source-spot on time) utilized of imaging system 100 can be 80%. The source of imaging system 100 can have a power rating of 50 kW. Compared to a 85 kW tube, this reduces the number of photons by a factor of 0.59. Imaging system 100 can have a slightly shorter focus-to-detector distance giving it a factor of 1.17 advantage.

Imaging system 100 does not rely on the anti-scatter grids used in conventional CT systems to reduce scattered radiation in the projection images. As discussed earlier, imaging system 100 takes advantage of the significantly smaller detector compared to a conventional system. Scatter scales approximately with the detector size assuming a constant distance between patient and detector. The smaller detector of imaging system 100 can be a significant advantage as the amount of scatter scales with the illuminated volume that, for a fixed object, is proportional to the detector area. The amount of scatter can be less than 10% for imaging system 100 while for a conventional system scatter exceeds 40% In a conventional system, scatter is managed with an anti-scatter grid, whereas in imaging system 100, an anti-scatter grid will not be necessary. The efficiency is about 75%. Imaging system 100 can have a significantly lower scatter fraction and can be operated without an anti-scatter grid, giving a photon advantage of 1.33.

Detector 110 can be photon counting, having an intrinsic DQE advantage of 20%. Additionally, photon counting detectors have a bias towards lower energies giving another 20% advantage. Thus, fewer photons are needed for the same image quality and can be counted as a (virtual) flux increase of a factor 1.44.

The transmission anode of imaging system 100 can provide 1.7 times as many photons for the same current as the more traditional steep-angle reflection anode.

Because imaging system 100 can adjust the number of photons depending upon the thickness of the object on a view-by-view, or even beam-by-beam, basis, a significant increase in maximum number of photons can be obtained. An average increase of a factor of 4 can be achieved.

The following table summarizes the cumulative advantages and disadvantages, and shows that the number of available photons is comparable to that of a standard point source system.

| IGCT/Standard | Cumulative | IGCT property relative to standard point source |
| --- | --- | --- |
| 0.15 | 0.15 | smaller detector area |
| 0.80 | 0.12 | lower duty cycle for IGCT |
| 0.59 | 0.07 | less tube power |
| 1.17 | 0.08 | shorter source-detector distance |
| 1.33 | 0.11 | operation without AS grid |
| 1.44 | 0.16 | photon-counting detector |
| 1.70 | 0.27 | transmission anode |
| 4.00 | 1.08 | virtual bow-tie |

The duty cycle can be increased to 100%. Imaging system 100 can use multiple tubes that can be alternated thus filling in the off-time of a single source. In addition, both iterative reconstruction and energy resolving detectors can improve performance. Overall, imaging system 100 can increase the effective number of photons by more than a factor of two.

Some of the effects discussed previously convert directly into dose savings to the patient. Imaging system 100 does not rely on the anti-scatter grids used in conventional CT systems. Anti-scatter grids are positioned after the patient and also prevent a significant percentage of the radiation from reaching the detector. Thus removing the anti-scatter grid reduces the dose to the patient. The omission of anti-scatter grids, and similarly, the removal of the dead-space between detector elements, leads to about a 25% improved dose efficiency.

The implementation of an adaptive filter can be used with inverse geometry CT and imaging system 100. The effective intensity of each source-spot-to-detector beam can be adjusted depending on the patient thickness, or attenuation, for that beam. This adaptive approach also minimizes irradiation where no body parts are present. A dose saving on the order of a factor of two can be achieved. Photon counting detectors provide an additional dose savings of a factor of 1.44.

The combined dose saving with imaging system 100 is almost a factor of 4. Even further dose savings can be achieved with the use of an energy resolving detector and iterative reconstruction methods. Imaging system 100 can be used only to scan the organ of interest and thereby further reduce the dose to the patient.

Figure 7:
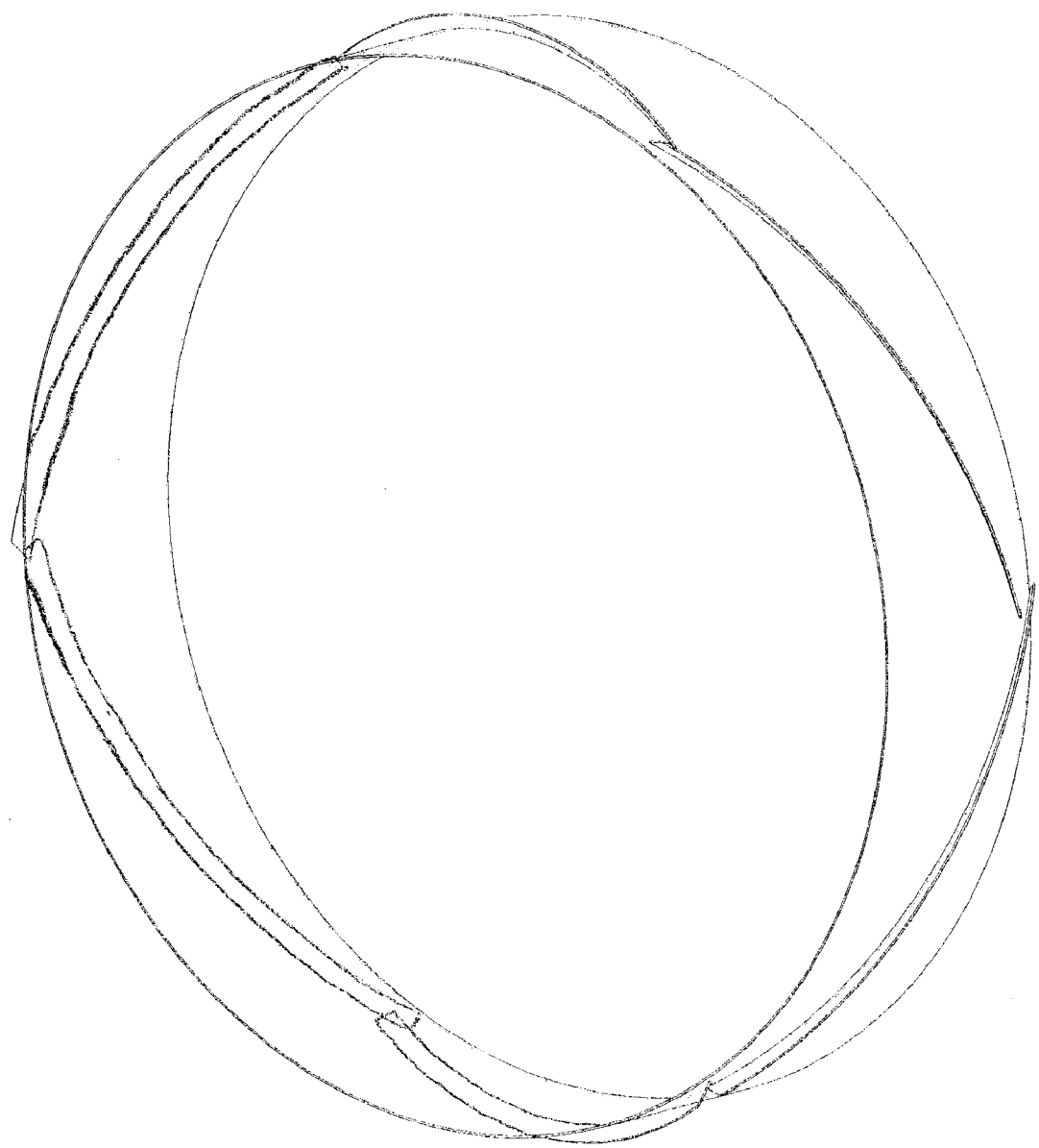
FIG. 7 is a diagram showing an exemplary source ring with linear sources of one embodiment of the present invention.

FIG. 7 is a diagram showing an exemplary source ring with linear sources of one embodiment of the present invention. Rather than using a two-dimensional array of sources, the source ring uses lines of sources. These linear sources can be constructed using either transmission targets or reflection targets. An array of linear X-ray tubes is arranged in a ring. Detector-collimator assembly rotates inside the ring.

Figure 8:
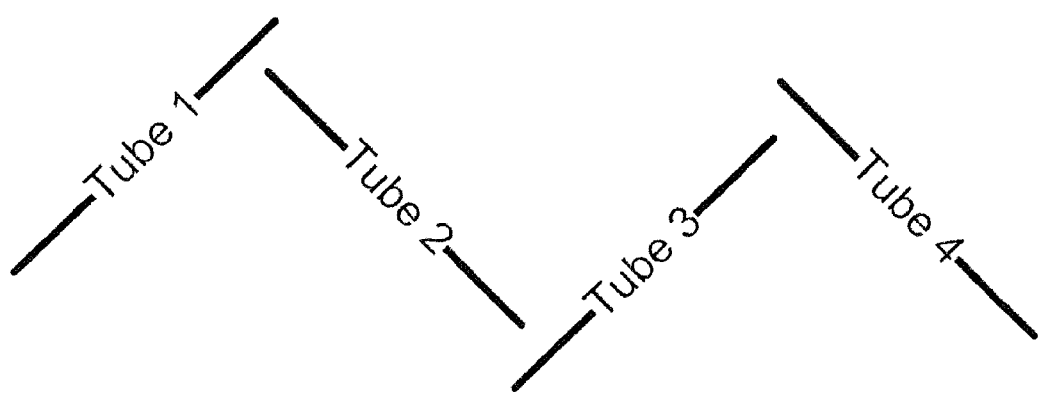
FIG. 8 is a diagram showing an exemplary arrangement of sources of one embodiment of the present invention.

FIG. 8 is a diagram showing an exemplary arrangement of sources of one embodiment of the present invention. An array of linear x-ray tubes is arranged in a ring. Detector-collimator assembly rotates inside the ring. This arrangement of source-spots can achieve complete sampling as the gap between any two linear sources is covered by a third linear source as shown in FIG. 8. Every plane intersecting the ring also intersects a source trajectory. As an example, although the dashed line lies in the gap between tube 2 and 3, it intersects tube 4 of FIG. 8. Another advantage is that the tube target, whether transmission or reflection, can be at a steep angle with respect to the X-ray beam. This allows a line-focus electron beam to be used which, in turn, enables a four-fold increase in tube power. The area source approach has advantages with the heat loading of the target and that implementation of the virtual bowtie is easier.

Imaging system 100 can have numerous advantages compared to conventional point source CT systems. Imaging system 100 can have lower dose and can be four-fold more dose-efficient than conventional point source systems. Imaging system 100 can have faster volume acquisition with scan times less than 300 msec. Imaging system 100 can perform whole-organ imaging with no table translation and no cone-beam artifacts. Data can be reconstructed using existing algorithms. Thus, advantages include fast acquisition and the reduction of dose, artifacts, and cost. Image quality can be comparable to standard point source CT and also have a significant margin to exceed current performance. Complete datasets can be produced and a variety of reconstruction algorithms can be used for efficient reconstruction.

A new type of scanning beam X-ray tube is disclosed that will enable inverse geometry CT with the promise of reducing radiation dose by at least a factor of four at comparable image quality as modern CT scanners.

Patient studies have shown that dose savings of a factor of 5 are possible with a system of an embodiment of the present invention. In addition, an adaptive exposure technique whereby the X-ray exposure is modulated depending on the local opacity of the patient can be used. Additional dose savings of more than 40% are possible; thus, potentially the system can operate at 9-fold lower dose than conventional systems.

Key to the advantages of inverse geometry imaging techniques are the availability of a large number (thousands) of X-ray focal spots distributed over a large area. Such an imaging geometry allows the reduction of the solid angle of the X-ray beam. Rather than projecting onto a large detector with a single X-ray source as is done in conventional imaging geometries, in inverse geometries the image is formed by many projections from the different X-ray focal spots onto a small detector. Hence, the solid angle of the X-ray beam is significantly reduced. The advantage is that scatter on the detector is significantly reduced as the scatter scales with the solid angle of the X-ray beam. Reduction in scatter reduces excess noise in the images and thus translates directly into dose reduction. Scatter reduction in inverse-geometry CT can translate into a dose saving of more than 40%.

Another advantage of small solid angles is that every projection image only samples a very small region of the imaging volume, therefore allowing for adaptive exposure. In other words, rather than exposing every part of the image with the same radiation dose, the exposure can vary depending on the opacity of the region exposed. For example, exposure can be reduced significantly in the lung field or thinner parts of the body and maintain exposure in more opaque regions. The dose savings potential of adaptive exposure in CT is even higher than in fluorosocopy and can achieve dose savings of more than 50%.

The small active area of the detector allows for cost efficient implementation of state-of-the-art detector technology. For example, photon-counting detectors have intrinsically better noise performance at low photon counts and a beneficial bias towards lower energies as compared to the energy-integrating detectors currently used in conventional CT systems. This can translate into dose savings of 20%.

An overall dose saving of a factor of 4 in inverse geometry CT (IGCT) can be achieved.

Earlier inverse-geometry CT designs envisioned rotating a large-area X-ray source array and a small detector at high speeds similar to 3rd generation CT scanners where a large detector and an X-ray source are rotated. Disadvantages of this approach are the need to rotate large masses at high speed, to have a high-power connection through a slip ring, and no access to cooling water at the X-ray source.

One embodiment of the present invention comprises a stationary ring of multi-focus X-ray sources with a stationary slot collimator. The ring of X-ray tubes can consist of a single vacuum envelope with one to 15 electron guns or of 1 to 15 separate vacuum envelops with individual electron guns or any combination of the former. Inside this ring, an annular sub-assembly can rotate, possibly consisting of a collimator on one side and a detector on the opposite side. The rotating collimator can have slots perpendicular to the slots of the stationary collimator ensuring collimation of the X-rays onto the detector. Advantages are the significant reduction of weight of the rotating assembly, elimination of high-power connections over slip rings and the availability of cooling water at the X-ray source.

Additionally, the target surface of the X-ray tube can be curved to conform to the collimator ring. A curved target with minimal inactive source area between adjacent X-ray sources can be used. These inactive areas can be chevron-shaped to minimize undersampling artifacts. The X-ray source can consist of a cathode assembly and a target assembly. The X-ray source can use a cathode assembly that generates, accelerates, and deflects the electron beam. The target assembly can consist of a beryllium window and a vacuum bell. The window may also be made of a material other than beryllium, such as thin stainless steel, titanium, carbon, any combination thereof, or any other material with a sufficiently low attenuation coefficient for X-rays to permeate and that can maintain the vacuum created within the bell. Alloys or combinations of the above materials or other materials can also be used. The vacuum bell creates the vacuum envelope between cathode assembly and window. A stand-alone tube with circular target and significant inactive area in the outer perimeter can be used. A tube that includes the chevron-shaped gap discussed earlier can also be used. Either a flat target, or a curved target that allows the use of a full ring of X-ray sources can be used.

Another engineering challenge can be the interface between the X-ray target and vacuum bell. Currently, this is done using a stainless-steel ring that is diffusion-bonded to the X-ray target assembly, which may, for example, consist of a thin-film tungsten target deposited on a beryllium window. This creates a relatively large inactive annular area around the X-ray target. The stainless steel ring is then welded to the vacuum bell. In one embodiment of the present invention, the window can be bonded directly to the vacuum bell to eliminate the inactive area of the stainless-steel ring. Electron-beam welding can be used with beryllium. It may also be used with a number of other potential window materials. Any other type of welding or bonding method may be used.

In other embodiments of the present invention, target materials include but are not limited to tungsten, copper, molybdenum, and alloys comprising these and/or other elements. A target may be deposited on a window, which as previously discussed may be beryllium, thin stainless steel, titanium, carbon, any combination thereof, or any other material with a sufficiently low attenuation coefficient for X-rays to permeate, e.g. a material comprising element(s) with atomic number(s) less than 30. The vacuum bell may stainless steel, copper, or other metals or alloys. A bonding method may be used which can attach the window to the vacuum bell directly. Depending on the materials of these two components, electron beam welding, brazing, or other methods may be used.

The target can be utilized up to 1 cm from the outer edge of the X-ray source. Beyond IGCT, sources that can be closely abutted can be used in other medical imaging applications such as image guidance, tomosynthesis, or radiation-therapy monitoring. A curved target with minimal inactive source area between adjacent X-ray sources can be used. A flat target with minimal inactive source area between adjacent X-ray sources can also be used. These inactive areas can be chevron shaped to minimize undersampling artifacts. Inactive areas can also be any other shape including but not limited to straight, curved, slanted, and so forth. The shape of the window, e.g. a beryllium window can match the shape of the target. For example, the shape of a beryllium window can be a curved window with chevron-shaped ends. Brazing and electron beam welding can be used as possible bonding methods. The vacuum bell and its overall shape can conform to the beryllium window shape. The X-ray tube can allow for accessibility of X-ray focal spots as close as 1 cm from the physical edge of the source.

Experiments can be performed with a pinhole that can be placed at different locations on the target surface. The electron beam can be steered on the transmission-target surface to illuminate the pinhole. As a baseline, the pinhole can be placed at the center of the target. The beam profile can be measured as projected onto the detector. The aluminum half-value layer of the beam and the fluence can be measured and compared to the established values. The pinhole can then be placed as close as 1 cm from the edge of the tube. The beam shape can be measured and the focus coils can be used to adjust the beam shape to match the profile in the center. The half-value layer of the beam and fluence can then be measured. If these values deviate from the values in the center, the pinhole can be moved further away from the edge of the tube and measurements repeated. This technique can establish how close to the edge spots can be accessed.

The scanning-beam digital X-ray system differs significantly from the design of a conventional fluoroscope. In contrast to a conventional fluoroscope, in which the X-ray tube has only a single focal spot, the scanning-beam digital X-ray tube is extended and consists of a scanning electron beam dwelling sequentially at up to 9,000 focal-spot positions. The X-ray tube technology is very similar to a CRT tube, but rather than using a phosphor target generating visible light from low-energy electrons, the scanning-beam digital X-ray tube uses a tungsten transmission target that generates X-ray photons from high-energy electrons. Other X-ray emissive targets including but not limited to molybdenum and copper can also be used. At each focal-spot position, X-ray photons are emitted towards the detector by use of a focusing collimator, thereby projecting a small view of the imaging volume.

In contrast to a conventional fluoroscope in which the detector is large and close to the patient, the scanning-beam digital X-ray detector is small and far away from the patient. The conventional fluoroscope uses an energy-integrating detector, while the scanning-beam digital X-ray system uses a photon-counting detector. These aspects can contribute to significant reduction in X-ray dose.

In conventional systems, the scatter fraction can be high and this problem can be addressed by the use of anti-scatter grids, which unfortunately can also reduce the primary radiation and thereby reduce dose efficiency. Even with anti-scatter grids, the detected scatter fraction in a conventional system can be as high as 56% for large patients. These scattered photons can contribute to the noise floor and degrade the contrast-to-noise ratios of images acquired by the system. In the scanning-beam digital X-ray system, the detector can be small and far away from the patient. Therefore, the scattered photons can have a much lower probability of reaching the detector. For the same large patient as described previously, the scanning-beam digital X-ray system can have a detected scatter fraction of less than 10%. The small scatter fraction in the scanning-beam digital X-ray system can allow for operation without an anti-scatter grid.

A photon-counting detector possesses a reduced noise floor that can be especially useful in imaging situations with low flux. Additionally, photon-counting detectors do not have a photon-energy bias as can be seen with energy-integrating detectors. In an energy-integrating detector, a 120-keV photon can produce twice as much signal as a 60-keV photon. In a photon-counting detector, both photons contribute equally to the signal. This enables lower-energy photons, which can generate high image contrast, to contribute more to the image than in a conventional system.

The peak voltage implemented by a conventional, e.g. regular point source geometry, fluoroscope system can range from 73 to 116 kVp in selected projections. Scanning-beam digital X-ray patient entrance exposures range from a reduction of 5-fold to a reduction of 10-fold relative to such systems. In general, scanning-beam digital X-ray contrast-to-noise compare favorably for exposures about 7-fold lower than that of the conventional point source exposure numbers, roughly in agreement with the 8-fold reduction observed in phantom studies. These exposure savings are equivalent to a 3.5-fold effective dose saving in patients.

Adaptive exposure—a new technique to save dose—can be implemented. Rather than exposing every part of the image with the same radiation dose, scanning-beam digital X-ray technology allows variation of the exposure depending on the opacity of the region exposed. Thus, exposure can be reduced in translucent areas such as the lung field and exposure can be maintained in more opaque regions.

A comparison of two images can be obtained from an anthropomorphic phantom mimicking a 90-kg male with and without adaptive exposure. The image with adaptive exposure can be imaged with 50% fewer photons than the image without adaptive exposure. Besides reducing the dose, adaptive exposure can also effectively compress the dynamic range of images and thereby improve image quality. With implementation of adaptive exposure the scanning-beam digital X-ray system can potentially produce equivalent image quality as conventional systems at 7-fold lower dose. Similar dose savings using inverse geometry in CT can be achieved.

In early proposed configurations of IGCT, the source array and detector array both rotated on a gantry.

An IGCT design with a stationary X-ray source array and a rotating detector can have powerful advantages. One advantage of such an IGCT system geometry is that all high-weight, high-voltage, and high-power components can be removed from the challenging environment of the rotating gantry. Thus miniaturization of the high-voltage power supply is not required; high-power slip rings are not required; the X-ray source array can be cooled with hospital water, eliminating the conventional gantry-mounted radiator and increased air-conditioning requirement; faster rotation times and faster volume acquisitions are possible; and overall reliability can be increased by the removal of many components, especially the X-ray source, from the high-G-force environment of the rotating gantry.

This IGCT design may require a total source array area that is approximately three times larger than previously proposed IGCT systems wherein both source and detector rotate.

An extended X-ray source array can be used with an inverse-geometry CT system with a large, e.g. 60 to 140 cm diameter, stationary ring of scanning X-ray source-spots. For some applications the source ring diameter may also be less than 60 cm or greater than 140 cm. However, in some embodiments of the present invention, the source ring diameter may be between 60 and 80 cm, 80 and 100 cm, 100 and 120 cm, or 120 and 140 cm, inclusive, or any other integer or non-integer number of centimeters within the enumerate ranges (e.g. 60, 65, 70, 75, 80, 85, 90, 95, 100, 105, 110, 115, 120, 125, 130, 135 or 140 cm) or any range between 60 and 140 cm.

As will be discussed later, the stationary ring of scanning X-ray source-spots can also be partially collimated by a stationary slot collimator. Inside the source-ring can be a rotating ring containing a detector and a collimator. This rotating ring, or gantry, can obtain power and output the detector signals through a slip-ring assembly. The collimator, which can be mounted on the rotating ring opposite the detector, can have a slot-pattern that focuses the X-rays onto the detector. The detector can without limitation be 4 to 14 cm by 8 to 24 cm, and the collimator can span an arc of about 60 to 160 degrees and can have a width of 8 to 24 cm. This system design can allow for rotation speeds of at least 0.5 rotations per second (rps) with image quality comparable to a conventional modern CT scanner. However, other dimensions and rotation speeds can also be used. The detector can be square, rectangular, trapezoidal, or any other shape. For example, the detector may be 10 cm by 10 cm but may also be 10 cm by 20 cm, or have any other square or rectangular dimensions, including but not limited to 4 to 14 cm by 8 to 24 cm. The collimator can focus radiation onto the detector, and may be curved to conform to the stationary collimator ring. It may span between 60 and 80 degrees, 80 and 100 degrees, 100 and 120 degrees, 120 and 140 degrees, or 140 and 160 degrees, inclusive, or any other number of degrees within the enumerate ranges (e.g. 60, 65, 70, 75, 80, 85, 90, 95, 100, 105, 110, 115, 120, 125, 130, 135, 140, 145, 150, 155 or 160 degrees) or any range between 60 and 160 degrees. Alternatively, for some applications, the collimator may span less than 60 degrees or more than 160 degrees.

Projection data can be acquired as the collimator-detector assembly rotates around the patient. The collimator can be located between the source array and the patient and source-spots can be active only when behind the collimator. The collimator may move only a small angular increment during the time the scan of every designated hole in the collimator is completed. A complete scan of the collimator may be described as a "superview". The maximum travel of the detector during an acquisition of a superview may be one detector width. A complete dataset can be obtained with as few as about 60 superviews.

As in fluoroscopy, the dose savings can be achieved by scatter reduction, superior detector technology and adaptive exposure.

Scatter reduction may be significant in inverse geometry systems. Inverse geometry CT does not rely on the anti-scatter grids used in conventional CT systems to reduce scattered radiation in the projection images. As discussed earlier, IGCT takes advantage of the significantly smaller detector compared to a conventional system. Scatter scales approximately with the detector size assuming a constant distance between patient and detector. Thus, in the IGCT system scatter impinging onto the detector is about 8% of that of a conventional system. In a conventional system scatter can be managed with an anti-scatter grid; in the IGCT system an anti-scatter grid may not be necessary.

Operation without an anti-scatter grid can translate into significant dose savings as anti-scatter grids can have a reduced transmissivity and block a large fraction of the primary X-rays. Transmissivity can be expressed in terms of the primary transmission factor $t_p$ of an anti-scatter grid. The ability of the anti-scatter grid to reject scatter can be quantified with the scatter transmission factor $t_s$, expressing how much of the scattered radiation impinging on to the grid is actually transmitted. Thus, relatively low values of the scatter transmission factor $t_s$ may be desirable. In general, the scatter transmission factor $t_s$ scales with the primary transmission factor $t_p$. In the following, the primary transmission factor $t_p$ that would match the scatter transmission factor $t_s$ of 8%, one approximation of the transmission factor $t_s$ that an IGCT system can achieve without an anti-scatter grid, can be calculated. A relationship between $t_s$ and $t_p$ can be calculated from the scatter-to-primary ratio without grid (SPR) and with grid ($SPR_g$):

$$t_s = \frac{SPR_g}{SPR} \cdot t_p.$$

For the calculation, the data of Chan et al, who used a 17-cm-thick water phantom and measured a scatter-to-primary ratio of 3.81 without anti-scatter grid can be used. The use of an anti-scatter grid with a primary transmission factor $t_p$ of 50% can be reduced that to an $SPR_g$ of 0.24. Thus, 6% can be derived as the corresponding value of $t_s$.

A grid with a transmission factor of 64% can yield a significantly higher $t_s$ of 14%. Thus, to achieve a $t_s$ of 8% an anti-scatter grid with $t_p$ of 54% would have to be used. However, in CT applications a higher scatter to primary ratio can be expected than measured by Chan et al. For example, scatter rejection can get slightly more efficient with higher scatter-to-primary ratios. Doubling of the SPR could lead to a 10-15% improvement in scatter rejection compared to that calculated above. Scatter rejection in IGCT may be comparable to use of an anti-scatter grid in a conventional system with a primary transmission factor $t_p$ of 60%. Thus, intrinsic scatter rejection in IGCT can increase the dose efficiency by 1.7-fold.

In pediatric imaging the use of an anti-scatter grid may not be beneficial as scatter may be low. In fact, where possible it is recommended to remove the anti-scatter grid. This may not be possible in conventional CT; particularly in pediatric imaging IGCT may be of great advantage to dose savings.

In the IGCT system, a photon-counting detector can be used. Compared to energy-integrating detectors, the noise performance of photon-counting detectors can be better. This is particularly true in a low count regime as is often encountered in very opaque regions of the patient. Additionally, photon-counting detectors can have a bias towards lower energies, thus offering better contrast resolution. The stopping power, e.g. X-ray photon-stopping power, of the detector can be comparable to conventional CT detectors. Thus, fewer photons may be needed for the same image quality and can be counted as a (virtual) flux increase of a factor of 1.2.

IGCT can allow the implementation of global and local adaptive exposure. Local adaptive exposure can vary exposure locally, e.g. depending on the opacity of the tissue scanned. Global adaptive exposure can be the overall change of the scan pattern, e.g. depending on the global shape of the patient. The effect can be similar to a bowtie filter used in CT imaging. In contrast to a bowtie filter, global adaptive exposure can be adjusted with the view angle.

Long path lengths, e.g. relatively long distances photons must travel through patient volume before reaching a detector, can lead to high attenuation of the incident beam, which can lead to low count rates. The majority of source positions lead to count rates that are at least ten times higher than the lowest count rate. Using adaptive exposure, acquisition times can be increased in low-count-rate areas and decreased in high-count-rate areas, thereby equalizing the number of detected photons. In an ideal case, the acquisition times of most source positions (90%) could be reduced to 10% of those in the low-count-rate areas. However, realistic implementation of a virtual bowtie may provide somewhat less acquisition-time savings. Acquisition-time savings of a factor of five can be achieved. However, dose savings can be much less since a significant fraction of the global adaptive exposure may occur outside the patient. The combined dose savings from local and global adaptive exposure can be larger than a factor of 2.

The scan patterns generated with adaptive exposure can preserve the overall timing and angular sampling of the CT scan. One implementation involves not changing the total number of illuminated collimator holes per superview. For example, the same number of holes per superview can be illuminated as are illuminated in a scan implemented without adaptive exposure. Illumination patterns for interleaved superviews can provide an increased flux in the central region of the collimator. The use of different illumination patterns can provide a two-dimensional adaptive filter. Several schemes for selecting the distribution of illumination are possible. For example, the illumination for one superview can be based on the results of the previous superview.

The combined dose-savings effect from local and global adaptive exposure can be at least a factor of 2, and potentially higher as the dose savings from local adaptive exposure can be as high as 2-fold by itself. In conclusion, the combined dose savings from scatter reduction, detector technology and adaptive exposure may be at least 4-fold.

An IGCT system of one embodiment of the present invention may not produce as many photons as modern, regular geometry point source CT scanners. As pointed out earlier, reduction in solid angle provides the significant design advantages in IGCT. However, reduction in solid angle can also lead to reduction in available photons with otherwise comparable operational parameters. The combination of scatter reduction, adaptive exposure, and a more efficient detector may allow the use of photons more efficiently.

The detector of a standard, e.g. regular geometry, point source CT system may be is 32 cm wide and 90 cm long. The IGCT system of one embodiment of the present invention has a detector size of 6 cm by 16 cm. Thus, the IGCT detector area in this embodiment may be 0.08 of another point source CT detector.

The duty cycle (the source-spot "on" time) of a scanning-beam digital X-ray system may be 80% compared to 100% in a standard, e.g. regular geometry, point source system.

A standard, e.g. regular geometry, point source CT system may have a power rating of 75 kW. The source of one embodiment of the present invention can operate at 25 kW. A standard point source system may operate at 3 rps—a rotation speed mainly geared towards cardiac CT. With cancer imaging, rotation speeds of 1.5 rps can be sufficient. (The number of photons in IGCT may be reduced by a factor of 0.67.) Scanning beam sources can operate up to 50 kW or even 75 kW, and can operate at rotation speeds including 3 rps.

An IGCT system may have a slightly shorter focus-to-detector distance than a regular-geometry point source system, giving the IGCT system a factor of 1.2 advantage.

As discussed, the smaller detector can lead to significantly reduced scatter in the projection images and allow for operation without anti-scatter grid. An increase in photon count by 1.67 can be achieved. As also discussed earlier, superior detector technology can provide equal image quality at lower photon flux. This factor can be 1.4.

The transmission anode of an IGCT system in one embodiment of the present invention can provide 1.7 times as many photons for the same current as a traditional steep-angle reflection anode.

As discussed, adaptive exposure can enable implementation of more efficient scan patterns. An average increase of a factor of 5 can be achieved.

The cumulative advantages and disadvantages, summarized in Table 1Error! Reference source not found., show that the number of available photons is comparable to that of a standard, e.g. regular-geometry, point source system.

TABLE 1

IGCT system properties compared to regular-geometry point source system

| IGCT/Standard Point Source System | Cumulative | IGCT property relative to Standard Point Source System |
|---|---|---|
| 0.08 | 0.08 | smaller detector area |
| 0.80 | 0.06 | lower duty cycle for IGCT |
| 0.67 | 0.04 | less tube power |
| 1.20 | 0.05 | shorter source-detector distance |
| 1.70 | 0.09 | operation without AS grid |
| 1.40 | 0.13 | photon-counting detector |
| 1.70 | 0.21 | transmission anode |
| 5.00 | 1.07 | adaptive exposure |
| Equivalent Photon Count | 1.07 | Advantages offset photon loss |

The duty cycle of an IGCT system in one embodiment of the present invention can be increased to 100% of the duty cycle of a conventional, e.g. regular geometry, point source CT system. The IGCT system can use multiple tubes that can be alternated thus filling in the off-time of a single source. In addition, both iterative reconstruction and energy resolving detectors can improve performance.

Overall, other implementations of IGCT can increase the effective number of photons by more than a factor of two compared to the numbers in Table 1.

IGCT data of embodiments of the present invention can be used with iterative-reconstruction methods. In the past, these methods have not been used for CT. However, incorporation of fast computing platforms may make it possible to reconstruct large datasets, e.g. IGCT datasets, in reasonable times.

Maximum Likelihood Expectation Maximization (MLEM) may be utilized to reconstruct datasets from unconventional geometries. An MLEM-based method can be less prone to under-sampling artifacts and reduce noise compared to standard methods. For example, iterative-reconstruction methods can cut the dose in CT scans by one third; iterative-reconstruction methods may be able to create better images from less complete dataset, relative to back-projection or other standard methods, such that fewer detected photons may be required to populate a dataset sufficient for reconstruction.

In summary, dose savings of at least 4-fold can be achieved.

The purpose of a collimator is to collimate X-rays emitted from the source onto the detector. In one embodiment of the present invention, a collimator can be separated into two subsystems: a stationary collimator ring and a rotating collimator arc. An advantage is that the rotating collimator arc can be relatively lightweight; thus, it can reduce the weight of the subsystem that rotates at high speeds. In addition to collimation, the collimator can serve as a containment structure for water cooling of the X-ray target. Water cooling can be sandwiched between the target and a window that will be mechanically supported by the ring collimator. The window may comprise a layer of thin aluminum, or any other thickness and material which can contain the cooling water while allowing X-rays to propagate from the target screen to the collimator. For example, the window may also be a layer of very thin stainless steel, copper, titanium, metal alloy, alloy, or any other material.

The stationary collimator ring can consist of a number of slots perpendicular to the central axis and extending over the entire length of the ring. The number of slots may be 10, 11, 12, 13, 14, 15, or any other number of slots up to 50 slots or any range between 10 and 50. For example, in one embodiment of the present invention, the stationary collimator ring comprises 16 slots. Each slot can be angulated and designed to collimate the X-rays onto the X-ray detector along the short dimension of the detector. Collimation along the long dimension can be achieved with the rotating collimator arc. The short dimension of the X-ray detector may be the dimension parallel to a central axis through the stationary collimator ring, and the long dimension of the X-ray detector may be the dimension perpendicular to the central axis, e.g. around the stationary ring.

The stationary collimator ring may be fabricated of an X-ray attenuating material. The number of rings may be 6 to 201 (e.g. creating 5 to 200 slots), inclusive, or any other number of rings therein or any range between 6 and 201. An X-ray attenuating material may have an atomic number between 11 and 83, inclusive. It may be a material of an atomic number between 11 and 38, inclusive, for sufficient attenuation in most cases, or a material of an atomic number between 39 and 83, inclusive, for relatively stronger attenuation or any range of atomic numbers between 11 and 83. Rings comprising a material of an atomic number between 39 and 83 may be relatively thinner than rings comprising a material of an atomic number between 11 and 38. For example, lead, copper, brass, or any other attenuating material or combination of materials may be used.

As discussed later, the stationary collimator may also provide stabilization and support for a cooling fluid system against the X-ray source target. Collimator ring material may have a high value of Young's modulus in order to provide this support. (The stiffness of a material relates to the amount of strain, e.g. the amount of deformation relative to its original dimensions, exhibited by the material when an external stress is applied and can be characterized by a quantity called Young's modulus.) The Young's modulus of the material may be at least 200 GPa. Alternatively, a material with Young's modulus of 150, 150-185, 159, 181, 193, 200, 190-210, 207, 248, 276, 287, 329, 345, 400-410, 435, 450, 450-650, 517, 550, 1000, 1050-1200, 1220 GPa or values between 150 and 1220 GPa or any range between 150 and 1220 GPa can be used. Carbon fiber, diamond, silicon carbide, steel, tungsten, tungsten carbide, iron, silicon, beryllium, molybdenum, sapphire, osmium, graphene, chromium, iridium, tantalum, or other materials can be used. For example, in one embodiment of the present invention, the stationary collimator comprises 17 stainless steel rings.

Fabrication of a collimator by machining and assembling rings may be compared to prior multi-focal spot collimator fabrication methods, which may have comprised electrical discharge machining, chemical etching, and other more complicated processes. In addition to the additional freedom of position and in-use advantages provided by slot collimators for IGCT, they may be significantly less labor-intensive or costly to fabricate.

Some or all slots on the stationary collimator may be sized and angulated such that an X-ray beam from an underlying focal spot may illuminate the entire face of a detector in the short dimension of the detector. Alternatively, some slots may be narrower or more steeply angulated such that X-ray beams from underlying focal spots illuminate only a portion or subset of the detector in the short dimension. The option of illuminating portions or subset of the detector face rather than the entire face may be particularly useful for the implementation of adaptive exposure; for example, subsets of an image volume may be illuminated more frequently, e.g. by all available focal spots, whereas other subsets may not be illuminated when focal spots within a narrowly collimated row are fired. It may also provide a manner of controlling the field of view of the system, e.g. decreasing the field of view by only firing focal spots within narrowly collimated rows.

Variations in the sizing and angulation of rows as described may follow a smooth continuum or may be in any other predetermined order, for example, "randomly" distributed in appearance.

The rotating collimator arc can extend over an arc of 60 to 160 degrees. It can also have slots, but the slots may be oriented perpendicular to the slots of the stationary collimator ring. Thus, this collimator collimates the X-rays along the long dimension of the X-ray detector. The "rotating" collimator arc does not necessarily need to rotate through 360 degrees for a given application, though it may rotate through 360 degrees or more in some embodiments of the present invention. It may move or slide along the stationary collimator ring though any number of degrees between 60 and 160 degrees or any range between 60 and 160 degrees in embodiments of the present invention.

Figure 9:
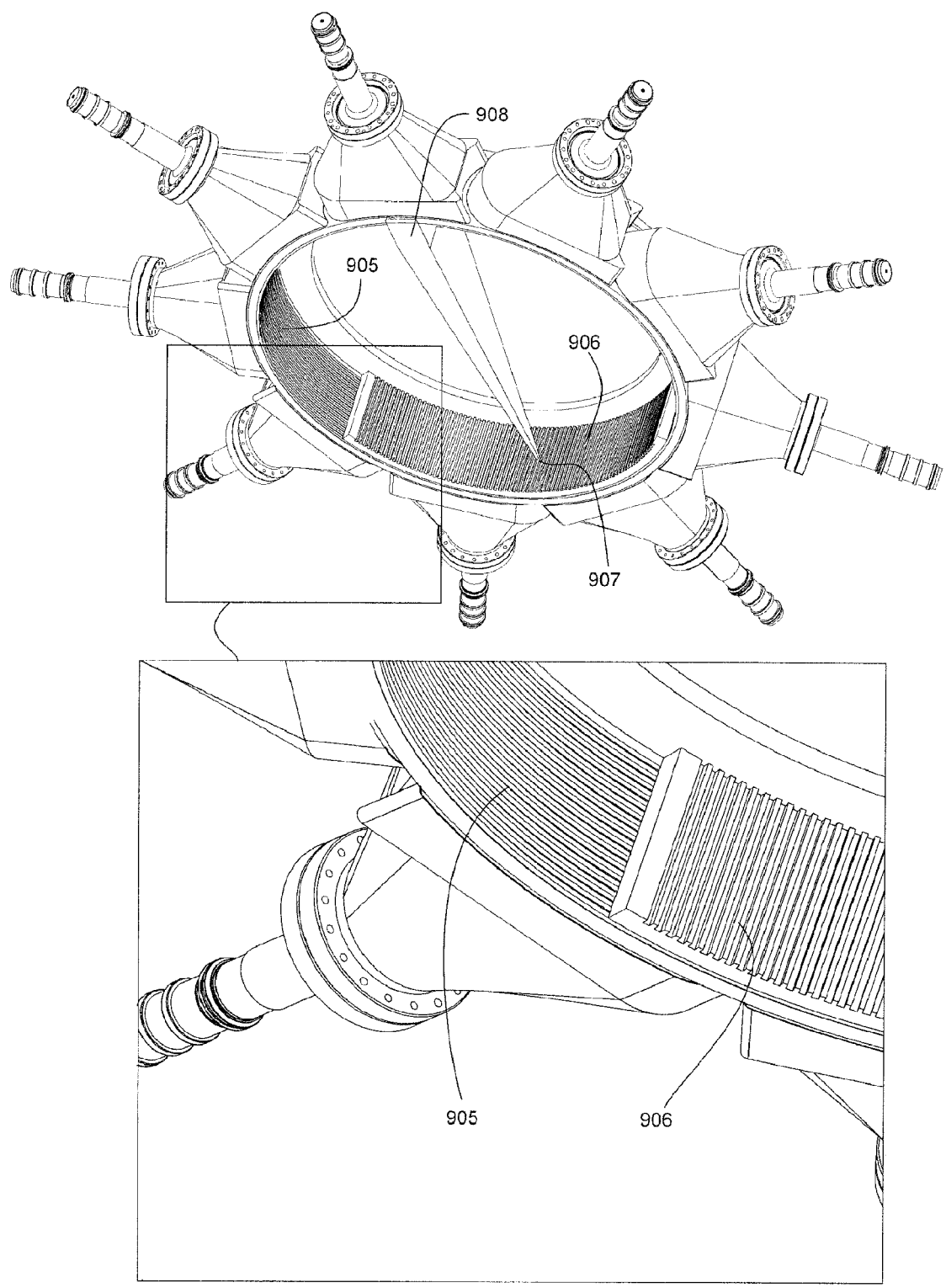
FIG. 9 is a diagram illustrating a stationary collimator ring and rotating collimator arc of one embodiment of the present invention.

FIG. 9 is a diagram illustrating a stationary collimator ring and rotating collimator arc of one embodiment of the present invention. In FIG. 9, stationary collimator ring 905 comprises slots subtending 360 degrees around a central axis, e.g. central to the ring, whereas collimator arc 906 comprises relatively short slots aligned parallel with a central axis. The overlap of collimator slots between stationary collimator ring 905 and collimator arc 906 may produce a pattern of collimator holes, e.g. collimator hole 907, as previously described. Collimator hole 907 can illuminate detector 908.

An IGCT scan can be performed by rotating the collimator arc inside the collimator ring. At every position of the collimator arc, the combination of slots of the collimators can form holes that precisely collimate the X-ray beam onto the X-ray detector. The overlap of the stationary and rotating collimators may create square holes, possibly of side length between 0.5 mm and 1 cm. Holes may be square, rectangular, or diamond-shaped. Side lengths may include but are not limited to 1 to 10 mm, 10 to 20 mm, 20 to 30 mm, 30 to 40 mm, 40 to 50 mm, 50 to 60 mm, 60 to 70 mm, 70 to 80 mm, 80 to 90 mm, and 90 to 100 mm, inclusive, or any other length within the enumerate ranges or any range between 0.5 mm and 1 cm. Side lengths may also include 0.5 to 2.5 mm, 2.5 to 5.5 mm, 5.5 to 7.5 mm, 7.5 to 9.5 mm, 9.5 to 11.5 mm, 11.5 to 13.5 mm, 13.5 to 15.5 mm, 15.5 to 17.5 mm, 17.5 to 19.5 mm, 19.5 to 21.5 cm, inclusive, or any length within the enumerate ranges or any range between 0.5 to 21.5 cm. As the collimator arc is rotating the collimator holes are moving in time across the surface of the collimator ring.

The electron beam and the resulting X-ray beam can move quickly compared to the collimator rotation speed. In such embodiments of the present invention, superviews can be generated quickly relative to collimator motion. For example, in one embodiment the overlap of the stationary collimator ring and rotating collimator arc can create 400 collimator-hole positions, the scanning of which can generate a superview within 0.5 ms. If the collimator arc and detector are operated at a rotation speed of 1.5 rps, the collimator may have moved 2.3 mm during the time, e.g. 0.5 ms, taken to complete a superview scan. Other embodiments can create and scan 100 to 2000 hole positions. Embodiments may have between 100 and 200, 200 and 300, 300 and 400, 400 and 500, 500 and 600, 700 and 800, 800 and 900, or 900 and 1000 holes, inclusive, or any number within the enumerated ranges or any range between 100 and 1000. For example, embodiments may have 300, 350, 400, 450, 500, 550, 600, or 650 holes.

To operate the scanner safely and efficiently, the X-ray beam should be aligned with the holes formed by the collimator ring and collimator arc. Alignment can be accomplished in two steps: First, the position of the X-ray beam may be established with respect to the rotating collimator at certain time points. Second, with knowledge of the beam position and the collimator geometry, the beam can be navigated to new collimator holes. As the collimator arc is moving, the navigation can take the collimator velocity into account. The velocity of the collimator arc can be monitored using LED-photodiode sensors or similar.

To measure X-ray beam position the collimator arc can be equipped with a small pixelated detector chip. For example, it may be equipped with a pixelated detector chip that is 1 cm$^2$, as small as 1 mm$^2$, as big as 6 cm$^2$, or any area in between. In some embodiments of the present invention the detector chip is 0.25 cm$^2$, 0.5 cm$^2$, 0.75 cm$^2$, 1 cm$^2$, 1.25 cm$^2$, 1.5 cm$^2$, 1.75 cm$^2$, 2 cm$^2$, or any other size between the enumerated values or any range between 1 mm$^2$ and 6 cm$^2$. It may be important to differentiate between the measurement of the beam position at startup of the scanner versus during the scan. At start up, the beam can be located on the detector in following way: the beam can be parked on the target at low power and highest permissible repetition rate. The collimator arc can rotate and at some point bring the detector into alignment with the X-ray beam. Once the beam is initially located, the detector can be repeatedly visited at the beginning of every scan of a superview, for example by calculating the expected position of the detector and aiming the X-ray beam to that location. With the detector illuminated, the centroid of the measured beam profile during a scan can be calculated. The centroid position can give the measured beam position, which can be compared with the calculated beam position, and the calculated beam position can be corrected for discrepancies.

This alignment scheme can be very stable as it can correct for actual beam position at a high frequency. Loss of alignment can be quickly detected and corrected or the scan can be aborted for patient safety.

Figure 10:
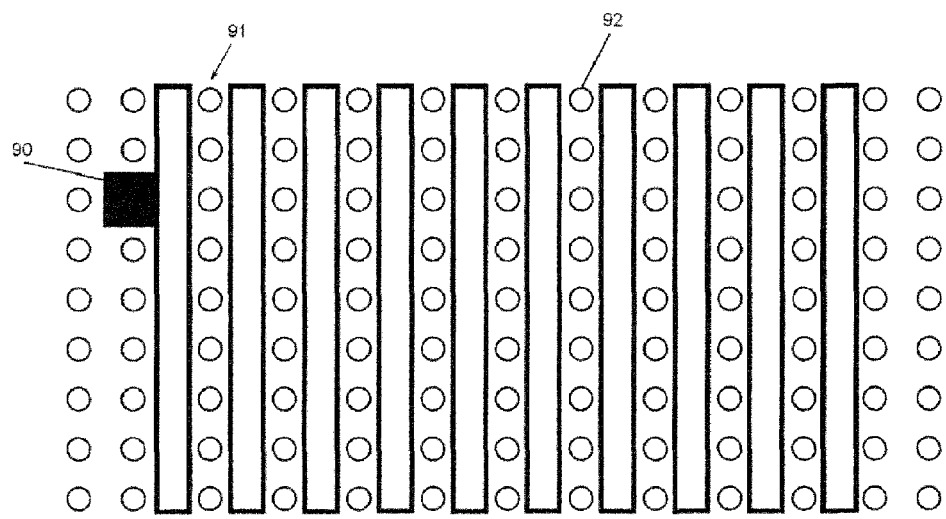
FIG. 10 is a diagram illustrating a collimator alignment configuration of one embodiment of the present invention.

FIG. 10 is a diagram illustrating a collimator alignment configuration of one embodiment of the present invention. In FIG. 10, parallel slots 91 align with beam spots, e.g. beam spot 92, such that an X-ray beam emitted at that beam spot can pass through the collimator. (For simplicity, perpendicular slots from the stationary collimator are not shown, though they may be present between rows of beam spots, e.g. perpendicular to parallel slots 91.) It may be important that only a beam spot within one of parallel slots 91 be illuminated, as an un-collimated beam spot may irradiate more area than intended for the imaging procedure and possibly provide an unhealthy amount of X-ray exposure to the person being imaged and/or surrounding personnel.

Detector 90 may be attached to the rotating collimator in one of parallel slots 91, on the edge of the rotating collimator, or in any other location on the collimator such that it can be periodically positioned over a beam spot. Periodically, e.g. once per superview, a beam spot aligned with the calculated position of the detector, based on the calculated position of the collimator, may be illuminated by the scanning beam. If the calculated position of the collimator is correct, or close to correct, detector 90 may receive some amount of radiation.

Figure 11:
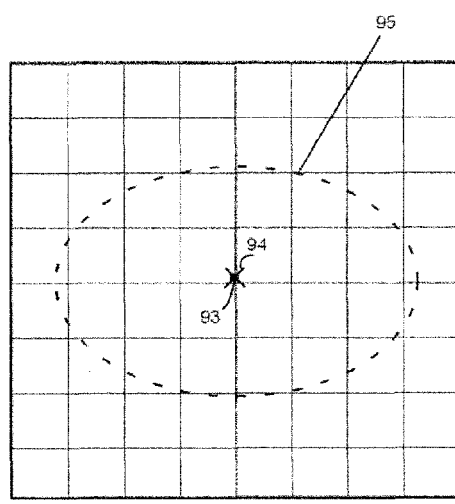
FIG. 11 is a diagram illustrating a signal from a detector with correct calculated collimator position in one embodiment of the present invention.
Figure 12:
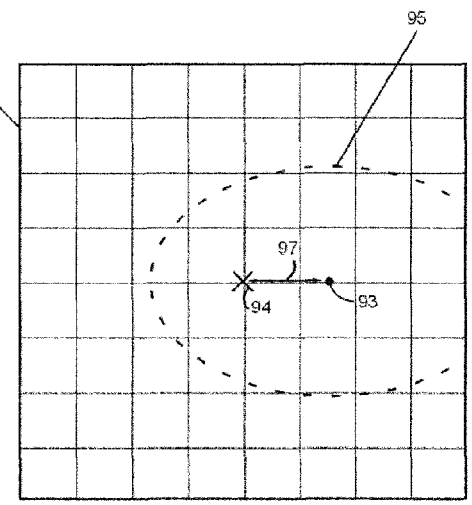
FIG. 12 is a diagram illustrating a signal from a detector with incorrect calculated collimator position in one embodiment of the present invention.

Detector 90 may be a pixelated or otherwise spatially resolved detector. FIG. 11 is a diagram illustrating a signal from a detector, e.g. detector 90, if the calculated collimator position was correct, in one embodiment of the present invention. When a focal spot is fired under a correctly calculated position for detector 90, centroid 93 of signal 95 may align with center 94 of detector 90 whereas if the detector position was incorrectly calculated, it may not. FIG. 12 is a diagram illustrating a signal from a detector, e.g. detector 90, if the calculated collimator position was incorrect, in one embodiment of the present invention. In FIG. 12, signal centroid 93 is not aligned with detector center 94. However, the distance of centroid 93 from detector center 94, the overall position of signal 95 on detector 90, or any other metric may be used to recalculate or recalibrate the assumed detector position. An interlock or safety system may be implemented such that X-ray emission can be shut off if centroid 93 is significantly non-aligned with detector center 94 or if no signal is detected by detector when the beam spot at the calculated detector position is fired.

In some imaging applications, a field of view smaller than entire width of the scanner may be desirable. To accommodate these applications, an additional set of slots or subset of slots that would illuminate a reduced width of the detector can be used, thereby reducing the field of view in the z-direction. As previously described, a subset or subsets of slots may be sized or angulated in a manner to illuminate only a portion of the detector width. Alternatively, an additional stationary collimator ring may be interchanged for or overlaid on the original.

The collimator may be constructed in a way that it sufficiently shields radiation not aimed at the detector. The goal of collimator design may be to maximize efficiency, minimize leakage (radiation penetrating the collimator) and spill (radiation through the collimator hole not captured by the detector). Further, the overall height of the collimator may be sufficient to minimize penumbra at the detector. Leakage of the collimator can be in the low-percentage range. Further reduction of leakage can be achieved by adding sheets of high-Z (high atomic number) material such as tungsten or lead.

In addition, the collimator can be designed to attenuate photon energies with upper limit as low as 10 keV and photon energies as high as 240 keV or any energies in between. The collimator can have 10 to 10,000 holes with a hole pitch, e.g. center-to-center spacing, between 1 mm and 10 cm. Hole pitch may be determined by the width of material strips or beams which form slots in the stationary collimator ring and rotating collimator arc. Hole pitch may be between 1 mm and 5 mm, 5 mm and 10 mm, 10 mm and 50 mm, 50 mm and 1 cm, 1 cm and 5 cm, 5 cm and 10 cm, inclusive, or any integer or non-integer length within these enumerated ranges or any range between 1 mm and 10 cm. For example, hole pitch may be 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm, or any number of millimeters between these enumerated values. Alternatively, hole pitch may be 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, or 1.5 cm, or any number of centimeters between these enumerate values.

The X-ray tube can run at acceleration voltages between 30 and 240 kVp. For example, maximum power in one embodiment of the present invention is 25 kW. In this embodiment, a maximum exposure of 11.5 Roentgen/min has been measured at 25 cm above the collimator. As discussed earlier, in an embodiment of the present invention an X-ray source can produce a sufficiently high flux to support an IGCT scan at 1.5 rps and can operate at 50 kW at 3 rps. Furthermore, the maximum high voltage can be increased to 240 kVp, and power levels can range from 5 kW to 125 kW.

Another aspect of embodiments of the present invention is spatial resolution and focal-spot size. The X-ray tube can enable full control over the focal-spot shape and size with sophisticated electron optics with focus and stigmation coils. A focal-spot size can be chosen that allows the system to produce sufficient spatial resolution for fluoroscopy systems and, at the same time, accommodate the thermal-load requirements of a given system. Spatial resolution requirements in CT may be less than in fluoroscopy. The IGCT system may produce superior spatial resolution compared to conventional, e.g. regular geometry, CT systems. In one embodiment of the present invention, wherein a high resolution detector is utilized, spatial resolution of 2.4 mm/lp can be achieved.

The X-ray target may be the dominant source of heat in the X-ray source, and cooling by direct contact with water can enable continuous removal of the full power load applied to the target. Additionally, backscatter of electrons from the target can result in a smaller, but significant heat load to other parts of the tube vacuum bell, where heat can also be removed by direct water cooling. The electronics that deflect and focus the electron beam may also be water-cooled. Finally, forced ambient air may be used to cool a ceramic insulator that may be included in tube design.

With the proper supply of cooling water and ambient air, the x-ray source in embodiments of the present invention can be used to operate at full power continuously in the normal environment of a hospital or imaging center.

The overall requirements for cooling water and HVAC for a cardiac fluoroscopy system built with the scanning-beam tube and for an IGCT system of one embodiment of the present invention may be: HVAC, 7000 BTU/hr and a water cooling supply running 20 gal/min intermittent, 30 psig drop from system inlet to outlet, 70 psia max pressure at either inlet or outlet, and 5 C to 15 C allowable temperature range.

As mentioned, most of the energy of the accelerated electrons may be deposited as thermal energy into the target layer of an X-ray source. Local and global heating of the target can be differentiated. The electron beam may heat the coating and immediate interface, e.g. window or beryllium window, rapidly. Further away from the electron-impact zone, heating may occur more slowly as the affected volume can be significantly larger. At distances of millimeters from the electron-impact zone, time constants of the heating can be long and the overall heating small. At the window-coolant interface, the problem can be largely treated as a steady-state problem globally affecting the heating of the system.

As indicated by thermal simulations, two important parameters for thermal performance may be the peak energy intensity ($J/m^2$) of the spot and the total power. The peak energy intensity of the spot can determine the maximum transient temperatures in the target, which can be limited by the melting temperature of the target materials. The total power can determine the global heating of the target and may need to be exceeded by the cooling capability of the system.

The local heat transfer can evolve in three distinct phases. First, the electron beam can impinge on the target for 1 µs. In this phase, the target coating, e.g. tungsten coating, can heat rapidly with negligible heat transfer to neighboring regions. In this phase, the thermal limits may largely be governed by the melting temperature of the target material, e.g. tungsten. In the second phase, heat may start spreading, decreasing the target coating temperature and increasing the temperature in the interface region. Limitations in this phase may be limits in the thermal properties of the interface region, e.g. beryllium window. In the third phase, after hundreds of microseconds the system may be largely equalized, but temperature can still be elevated. If it is desired to revisit the same focal spot in this timeframe, an offset temperature may be taken into account. For the scanning-beam digital X-ray system, a repetition rate of once every 300 µs can be achieved. For an IGCT source of some embodiments of the present invention, a repetition rate slower than once every 300 µs can be used. For example, in one embodiment of the present invention a repetition rate of once every 300 ms can be used. Alternatively, repetition rates of once every 50 ms, 100 ms, 150 ms, 200 ms, 250 ms, 300 ms, 350 ms, 400 ms, 450 ms, 500 ms, or any other number or fraction of milliseconds may be used or any range between 50 ms and 500 ms.

The transient heating of the target with electron-beam exposure can be studied in great detail using Monte Carlo and/or finite-element simulation. Incident electrons may deposit most of their energy thermally in the material, leading to significant heating of the target. Both the magnitude (power) of the electron heating as well as its spatial distribution within the target material can be inputs to the thermal analysis. The distribution of energy in the z-direction (perpendicular to the material surface) and in the radial direction (parallel to the material surface) can be characterized.

The distribution in the z-direction can depend on the energy of the incident electrons and the target material. For example, the z-profile of the thermal deposition in tungsten for various electron energies can be calculated using Monte Carlo simulations. An incident electron beam can be generated, e.g. simulated, and its component electrons traced throughout the target. The deposited energy of every event can then be tallied and histograms computed showing energy vs. depth. Electron beams up to 140 kVp can be studied. The penetration depth and the width of the depth profile peak may increase with incident electron energy. The majority of energy may be deposited within a 10-µm depth.

The spot size of the electron beam may be controlled by the electron optics of the electron gun. For some imaging applications, the spot size may be minimized as much as possible without exceeding the thermal limits of the target. Electron-beam spots may be described fairly well by a Gaussian profile.

In some embodiments of the present invention, power can be 50 kW. The spot dwell time can be 1 µs and the beam move time can be 0.25 µs. Alternatively, in the IGCT system of one embodiment of the present invention, the dwell time can be shortened to 0.25 µs, thus reducing the deposited energy per spot. To recover the reduced duty cycle, the firing of adjacent source tubes can be alternated; thus, while the scanning electron beam moves in one tube, the other tube fires and vice versa. However, in the IGCT system of another embodiment of the present invention, a power of 25 kW can be sufficient and the scanning-beam digital X-ray technology can be readily applied.

The thermal energy from every focal spot can ultimately reach the window-coolant, e.g. beryllium-coolant, interface and contribute to the global heat transfer of the system. Cooling can be sufficient to remove the heat from the entire system. The bulk cooling of the X-ray tube can be done by forced convection of cooling water that is injected in a thin layer between the substrate, e.g. beryllium, and the collimator. This cooling mechanism can ensure that the tube operates at steady-state temperature and thermal calculations can show that this cooling mechanism is sufficient to operate the X-ray tube constantly at a power of 45 kW. With a power limit of 25 kW, the system can run continuously at full power for many hours. For example, initial conditioning protocol of the tube may include full-power operation for 12 hours. The cooling capacity of forced convection can depend on the area it is applied to. Therefore, problems with the bulk cooling capacity of IGCT systems of embodiments of the present invention are unlikely, even if operated at higher powers, as the surface area of an IGCT system can be about 10 times larger than that of a scanning-beam digital X-ray tube.

For the IGCT X-ray source ring of one embodiment of the present invention, water cooling can be implemented that collectively cools the entire ring. Water can be injected into a thin layer between target and collimator from one side of the ring and water can be collected at the other side of the ring.

A fixed source ring with a two-tiered collimator can be used. Complete sampling can be produced and the CT data can be reconstructed. A slot collimator can be used and/or a rotating collimator detector assembly can be also used. In addition, rather than rotating, the collimator detector assembly can be rocked in a way that every slot in the rotating collimator can be illuminated. The object can then be mounted on a rotary stage. The combination of rocking the collimator and rotating the object can enable production of a complete data set. A drawback of this approach may be that with a source having a flat target, it may not conform to the rotating collimator. This drawback can be overcome by using just the central region of the source that can be closely positioned to the rotating collimator. Different acquisition strategies can be used and iterative-reconstruction algorithms can be used to reconstruct the data.

Scanning-beam X-ray digital systems can be used for interventional radiology and the field of view of a cardiology scanning-beam X-ray digital system can be increased. Rather than extending the source, two detectors can be used with a specialized collimator to illuminate both detectors. Two closely abutted X-ray sources can be used. Another area where the technology could be very beneficial is a stationary tomosynthesis system. Rather than rotating an X-ray source and detector, a large-area multi-focus X-ray tube array can be used and it can acquire images without movement of the components. This could offer real time 3-D images that can be used for image-guided procedures.

Figure 13:
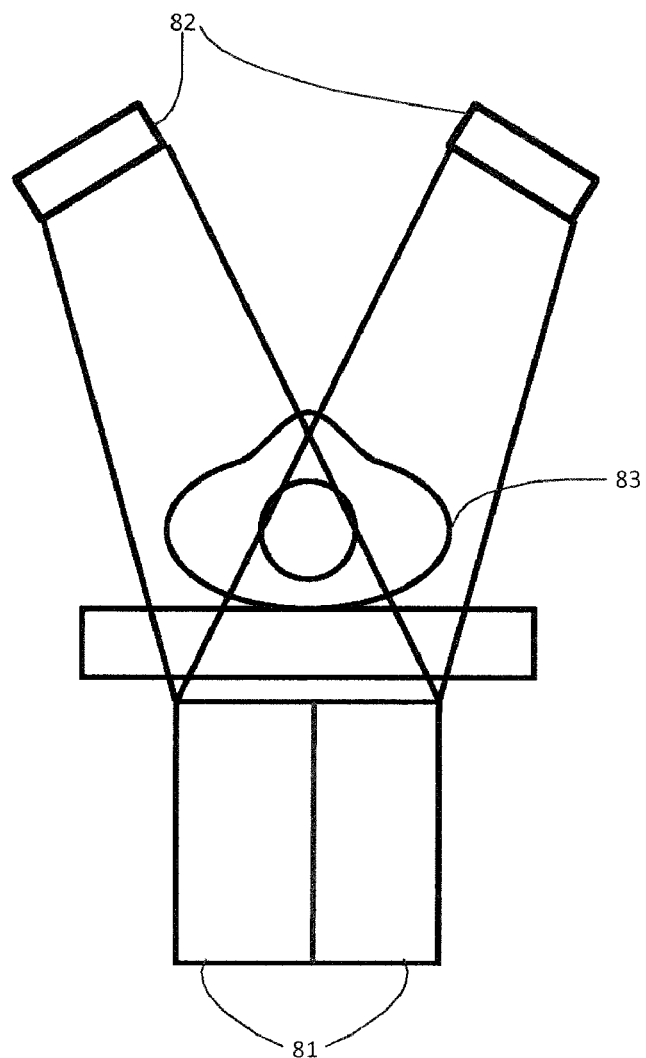
FIG. 13 is a diagram illustrating the illumination of two detectors by two closely abutted X-ray sources in one embodiment of the present invention.

FIG. 13 is a diagram illustrating the illumination of two detectors by two closely abutted X-ray sources in one embodiment of the present invention. "Abuttable" sources 81 can function as a single, large-area multi-focus X-ray source, or a single, large-area multi-focus X-ray tube can be used. They can be collimated by one or two collimators to illuminate detectors 82. Alternatively, they may be collimated to illuminate two, three, four, or more detectors. Two, three, four, or more sources can also be abutted and function as a single, large-area X-ray source for a further increased field of view. The field of view of the system may encompass patient 83 as shown. Even if abuttable sources remain stationary or closely abutted with one another during most or all imaging procedures, it may be more cost-effective to utilize abuttable sources of embodiments of the present invention in an imaging system requiring significant source area rather than a single source of said area; fabrication of large sheets of target material can X-ray sources can be difficult and costly.

These are only a few examples for the vast possibilities of extended multi-focus X-ray sources.

An IGCT system design of embodiments of the present invention can have the following advantages over existing high-performance conventional multi-slice systems: 4-fold lower dose than conventional CT, faster volume acquisition than helical CT, whole-organ imaging with no table translation and no cone-beam artifacts, and others. The scanning-beam digital X-ray system uses a large-area scanning X-ray source to project an X-ray beam through the patient onto a small-area, high-efficiency detector. A high-speed computer reconstructs multi-slice tomographic images in real time. This geometry and reconstruction can provide many substantial imaging and performance advantages as well as radiation-reduction advantages for the patient, physician, and fluoroscopy lab staff.

An inverse geometry CT system of embodiments of the present invention can use a fixed source ring and a rotating detector collimator assembly. It can also use: the combination of a stationary and a rotating collimator; the engineered gap to conform to Tuy's criterion; the use of a detector on the rotating collimator for alignment; the combination of perpendicular slots to form holes; and adaptive exposure. A compact high-power scanned-electron-beam X-ray sources with a large number of focal spots arranged in a two-dimensional array can be used.

Components of a scanning-beam digital X-ray source of embodiments of the present invention may be the cathode assembly, target assembly, collimator, shielding, cooling manifolds and mounting brackets. The X-ray source can share the same cathode assembly, but can use a significantly different target assembly. Collimator and cooling can be shared between the 9 sources, or other numbers of sources utilized. Mounting and shielding can be part of the overall gantry.

Figure 14:
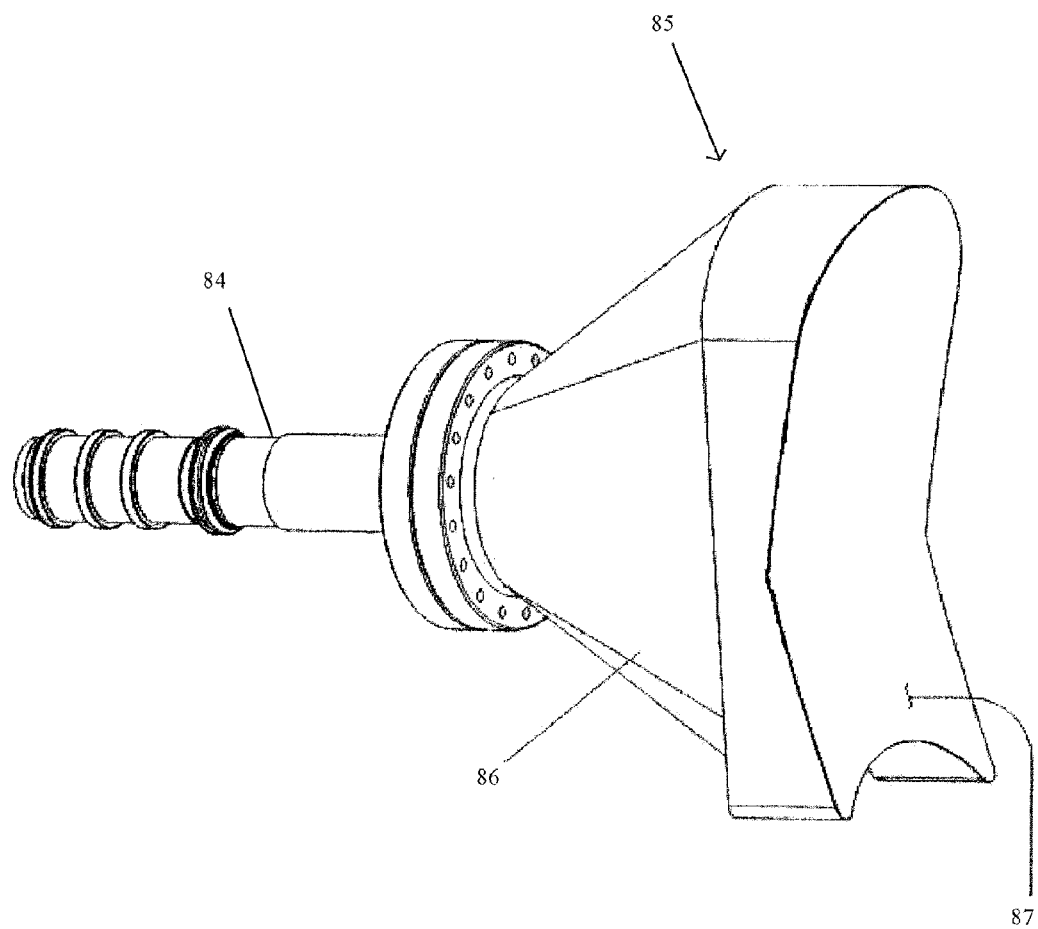
FIG. 14 is a diagram illustrating components of a scanning-beam digital X-ray source of one embodiment of the present invention.

FIG. 14 is a diagram illustrating components of a scanning-beam digital X-ray source of one embodiment of the present invention. Cathode assembly 84 may be attached to the target assembly 85, comprising target 87 within vacuum bell 86. As previously discussed, target 87 and the window of vacuum bell 86 may be curved to better fit around and align with a stationary collimator ring. The edges of target 87 may be flat, or may be chevron-shaped or curved, as in the embodiment of FIG. 14. Target 87 may be welded directly to vacuum bell 86 such that a very small amount of dead space exists on target 87, and the source can be closely abutted with other sources.

In another embodiment of the present invention, the fixed X-ray source ring comprises a single vacuum envelope with a continuous X-ray target. The envelope can house several electron guns that can illuminate the target in sequence.

The cathode assembly can consist of electron gun, acceleration anodes, gun and acceleration electronics, focus and deflection coils, focus and deflection electronics and the enclosure. The target assembly can consist of a vacuum bell and target. A vacuum bell may the intermediate part between acceleration anodes and target. The vacuum bell can be machined. The vacuum bell can also be casted.

In one embodiment of the present invention, the stationary collimator can have 16 slots, and it can be machined from stainless steel. Also, the collimator can be shared between the tubes. Similarly, cooling can be shared between the tubes.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An X-ray imaging system for imaging an object comprising:
   a vacuum bell for creating a vacuum envelope in an X-ray source;
   an X-ray radiation-permeable window configured to emit X-ray radiation from a plurality of spots;
   a collimator located between said X-ray source and said object for projecting said X-ray radiation through said object;
   an X-ray detector for measuring amount of said X-ray radiation passing through said object and striking said detector;
   a second vacuum bell in contact with said vacuum bell for creating a second vacuum envelope in a second X-ray source; and
   a second X-ray radiation-permeable window configured to emit X-ray radiation from a second plurality of spots.

2. The X-ray imaging system of claim 1 wherein said X-ray radiation-permeable window and said second X-ray radiation-permeable window are in contact with each other.

3. The X-ray imaging system of claim 1 wherein said plurality of spots is located less than 1 cm from an edge of said window.

4. The X-ray imaging system of claim 1 further comprising:
   a bonded connection between said window and said vacuum bell.

5. The X-ray imaging system of claim 4 wherein said bonded connection is a brazed bond.

6. The X-ray imaging system of claim 4 wherein said bonded connection is an electron beam weld.

7. A computed tomography X-ray imaging system for imaging an object comprising:
   a plurality of stationary X-ray sources forming a ring for producing X-ray radiation;
   a rotating X-ray detector positioned within said ring for measuring amount of said X-ray radiation passing through said object and striking said detector;

a stationary collimator located between said plurality of X-ray sources and said object;

a rotating collimator located between said plurality of X-ray sources and said object with a plurality of slots.

8. The computed tomography X-ray imaging system of claim 7 wherein said stationary collimator further comprises at least ten slots.

9. The computed tomography X-ray imaging system of claim 7 wherein said stationary collimator further comprises between 10 and 50 slots.

10. The computed tomography X-ray imaging system of claim 7 wherein said rotating slot collimator spans an arc between 60 and 160 degrees.

11. The computed tomography X-ray imaging system of claim 7 wherein said stationary collimator further comprises metal rings.

12. The computed tomography X-ray imaging system of claim 7 further comprising:

cooling water coupled to an X-ray target for removing heat generated by said X-ray target.

13. The computed tomography X-ray imaging system of claim 7 wherein said stationary collimator further comprises at least ten slots perpendicular to said plurality of slots.

14. The computed tomography X-ray imaging system of claim 7 further comprising a sensor for monitoring velocity of said rotating collimator.

15. The computed tomography X-ray imaging system of claim 7 wherein said plurality of X-ray sources operate at full power for at least one hour.

16. A method of aligning an X-ray beam in an X-ray imaging system comprising:

establishing a position of said X-ray beam with respect to a moving collimator at a plurality of time points;

navigating said X-ray beam to a calculated position of a hole in said collimator; and correcting alignment of said X-ray beam based on location of said X-ray beam on said detector.

17. The method of claim 16 further comprising:
aborting said X-ray beam if said X-ray beam is not aligned.

18. The method of claim 16 further comprising:
determining centroid position of said X-ray beam on said detector; and comparing said centroid position with a calculated centroid position for said X-ray beam.

19. The method of claim 16 further comprising:
monitoring velocity of said collimator.

20. The method of claim 16 further comprising:
calculating position of said detector based on said velocity and an initial position of said collimator.

* * * * *